US009718879B2

(12) United States Patent
Okuse et al.

(10) Patent No.: US 9,718,879 B2
(45) Date of Patent: Aug. 1, 2017

(54) METHODS OF TREATING PAIN BY INHIBITION OF VGF ACTIVITY

(71) Applicant: IMPERIAL INNOVATIONS LTD., London (GB)

(72) Inventors: Kenji Okuse, London (GB); Alessandro Pristera, London (GB); Andrew Rice, London (GB)

(73) Assignee: IMPERIAL INNOVATIONS LTD., London (GB)

( * ) Notice: Subject to any disclaimer, the term of this patent is extended or adjusted under 35 U.S.C. 154(b) by 110 days.

(21) Appl. No.: 14/374,732

(22) PCT Filed: Jan. 25, 2013

(86) PCT No.: PCT/GB2013/050162
§ 371 (c)(1),
(2) Date: Jul. 25, 2014

(87) PCT Pub. No.: WO2013/110945
PCT Pub. Date: Aug. 1, 2013

(65) Prior Publication Data
US 2014/0370024 A1    Dec. 18, 2014

(30) Foreign Application Priority Data

Jan. 26, 2012    (GB) .................................. 1201332.2

(51) Int. Cl.
| | | |
|---|---|---|
| A61K 39/395 | (2006.01) |
| C07K 16/22 | (2006.01) |
| C07K 16/28 | (2006.01) |
| C07K 16/18 | (2006.01) |
| G01N 33/566 | (2006.01) |
| A61K 39/00 | (2006.01) |

(52) U.S. Cl.
CPC ............ *C07K 16/18* (2013.01); *C07K 16/286* (2013.01); *G01N 33/566* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,969,108 A | 10/1999 | McCafferty et al. |
| 2008/0050342 A1 | 2/2008 | Fire et al. |
| 2009/0264411 A1 | 10/2009 | Laing et al. |
| 2010/0179124 A1 | 7/2010 | Johnson et al. |
| 2010/0197676 A1 | 8/2010 | Isshiki et al. |

FOREIGN PATENT DOCUMENTS

| | | |
|---|---|---|
| WO | 90/02809 A1 | 3/1990 |
| WO | 91/09967 A1 | 7/1991 |
| WO | 91/10737 A1 | 7/1991 |
| WO | 91/11172 A1 | 8/1991 |
| WO | 92/01047 A1 | 1/1992 |
| WO | 92/02551 A1 | 2/1992 |
| WO | 92/18619 A1 | 10/1992 |
| WO | 92/22853 A1 | 12/1992 |
| WO | 93/08829 A1 | 5/1993 |
| WO | 93/11236 A1 | 6/1993 |
| WO | 94/02518 A1 | 2/1994 |
| WO | 95/15982 A2 | 6/1995 |
| WO | 95/20401 A1 | 8/1995 |
| WO | 98/55148 A1 | 12/1998 |
| WO | 03/016475 A2 | 2/2003 |
| WO | 03/077914 A1 | 9/2003 |
| WO | 2004/051268 A1 | 6/2004 |
| WO | 2004/106377 A1 | 12/2004 |
| WO | 2005/003169 A2 | 1/2005 |
| WO | 2005/003170 A2 | 1/2005 |
| WO | 2005/003171 A2 | 1/2005 |
| WO | 2007/044084 A2 | 4/2007 |

(Continued)

OTHER PUBLICATIONS

Garry et al., "Varicella zoster virus induces neuropathic changes in rat dorsal root ganglia and behavioral reflex sensitisation that is attenuated by gabapentin or sodium channel blocking drugs", Pain, 2005, vol. 118, 97-111.
Hudson et al., "VR1 protein expression increases in undamaged DRG neurons after partial nerve injury", European Journal of Neuroscience, 2001,vol. 13, 2105-2114.
Anesti et al., "Efficient delivery of RNA interference to peripheral neurons in vivo using herpes simplex virus", Nucleic Acids Research, 2008, 36(14), 12 pages.
Shao et al., "A multi PDZ-domain protein Pdzd2 contributes to functional expression of sensory neuron-specific sodium channel Nav1.8", Molecular and Cellular Neuroscience, 2009, 42(3), 219-225.
Baker et al., "In vitro and intrathecal siRNA mediated Kv1.1 knock-down in primary sensory neurons", Molecular and Cellular Neuroscience, 2011, 48(3), 258-265.

(Continued)

*Primary Examiner* — Christine J Saoud
*Assistant Examiner* — Jon M Lockard
(74) *Attorney, Agent, or Firm* — McDonnell Boehnen Hulbert & Berghoff LLP

(57) ABSTRACT

The present disclosure relates to a method of treating pain, in particular neuropathic pain, comprising administering a therapeutically effective amount of an inhibitor of VGF activity resulting from binding of VGF or a peptide of the type TLQP-21 to the receptor qC1qR. The disclosure also relates to and methods of screening for said inhibitors.

12 Claims, 13 Drawing Sheets

(56) References Cited

FOREIGN PATENT DOCUMENTS

| | | |
|---|---|---|
| WO | 2009/093009 A1 | 7/2009 |
| WO | 2009/093013 A1 | 7/2009 |
| WO | 2010/121646 A1 | 10/2010 |
| WO | 2011/156588 A1 | 12/2011 |

OTHER PUBLICATIONS

Wallace et al., "The effect of the palmitoylethanolamide analogue, palmitoylallylamide (L-29) on pain behaviour in rodent models of neuropathy", British Journal of Pharmacology, 2007, vol. 151, 1117-1128.
Toshinai et al., "Neuroendocrine regulatory peptide-1 and -2: Novel bioactive peptides processed from VGF", Cellular and Molecular Life Sciences, 2009, 66(11-12), 1939-1945.
Bartolomucci et al., "TLQP-21, a VGF-derived peptide, increases energy expenditure and prevents the early phase of diet-induced obesity", PNAS, 2006, 103(39), 14584-14589.
Jethwa et al., "VGF-derived peptide, TLQP-21, regulates food intake and body weight in Siberian hamsters", Endocrinology, 2007, 148(8), 4044-4055.
Severini et al., "TLQP-21, a neuroendocrine VGF-derived peptide, prevents cerebellar granule cells death induced by serum and potassium deprivation", Journal of Neurochemistry, vol. 104, 534-544.
Lever et al., "Continuous infusion of the cannabinoid WIN 55,212-2 to the site of a peripheral nerve injury reduces mechanical and cold hypersensitivity", British Journal of Pharmacology, 2007, vol. 151, 292-302.
Zhu et al., Phosphoinositide-3-kinase and mitogen activated protein kinase signaling pathways mediate acute NGF sensitization of TRPV1, Mol. Cell. Neurosci., 2007, 34(4), 689-700.
Zhuang et al., "Phosphatidylinositol 3-kinase activates ERK in primary sensory neurons and mediates inflammatory heat hyperalgesia through TRPV1 sensitization", The Journal of Neuroscience, 2004, 24(38), 8300-8309.
Kayssi et al., "Mechanisms of protease-activated receptor2-evoked hyperexcitability of nociceptive neurons innervating the mouse colon", J. Physiol, 2007, 580(3), 977-991.
Bridges et al., "Localisation of cannabinoid receptor 1 in rat dorsal root ganglion using in SITU hybridisation and immunohistochemistry", Neuroscience, 2003, vol. 119, 803-812.
Farquhar-Smith et al., "Cannabinoid CB1 receptor expression in rat spinal cord", Molecular and Cellular Neuroscience, 2000, vol. 15, 510-521.
Obata et al., "TRPA1 induced in sensory neurons contributes to cold hyperalgesia after inflammation and nerve injury", The Journal of Clinical Investigation, 2005, 115(9), 2393-2401.
Christoph et al., "Antinociceptive effect of antisense oligonucleotides against the vanilloid receptor VR1/TRPV1", Neurochemistry International, 2007, 50(1), 281-290.
Verma et al., "Antibodies engineering: Comparison of bacterial, yeast, insect and mammalian expression systems", Journal of Immunological Methods, 1998, vol. 216, 165-181.
Angal et al., "A single amino acid substitution abolishes the heterogeneity of chimeric mouse/human (IgG4) antibody", Molecular Immunology, 1993, 30(1), 105-108.
Kohler et al., "Continuous cultures of fused cells secreting antibody of predefined specificity", Nature, 1975, vol. 256, 495-497.
Kozbor et al., "The production of monoclonal antibodies from human lymphocytes", Immunology Today, 1983, vol. 4, p. 72-78.
Babcook et al., "A novel strategy for generating monoclonal antibodies from single, isolated lymphocytes producing antibodies of defined specificities", Proc. Natl. Acad. Sci., 1996, vol. 93, 7843-7848.
Milstein et al., "Hybrid hybridomas and their use in immunohistochemistry", Nature, 1983, vol. 305, 537-539.
Traunecker et al., "Bispecific single chain molecules (Janusins) target cytotoxic lymphocytes on HIV infected cells", EMBO J., 1991, vol. 10, 3655-3659.
Brinkman et al., "Phage display of disulfide-stabilized Fv fragments", J. Immunol. Methods, 1995, vol. 182, 41-50.
Ames et al., "Conversion of murine Fabs isolated from a combinatorial phage display library to full length immunoglobulins", J. Immunol. Methods, 1995, vol. 184, 177-186.
Kettleborough et al., "Isolation of tumor cell-specific single-chain Fv from immunized mice using phage-antibody libraries and the re-construction of whole antibodies from these antibody fragments", Eur. J. Immunol., 1994, vol. 24, 952-958.
Persic et al., "An integrated vector system for the eukaryotic expression of antibodies or their fragments after selection from phage display libraries", Gene, 1997, vol. 187, 9-18.
Burton et al., "Human antibodies from combinatorial libraries", Advances in Immunology, 1994, vol. 57, 191-280.
Jiang et al., "Crystal structure of human p32, a douhnut-shaped acidic mitochondrial matrix protein", Proc. Natl. Acad. Sci., 1999, vol. 96, 3572-3577.
Bordin et al., "Fibroblast Heterogeneity of Signal Transduction Mechanisms to Complement-C1q. Analyses of Calcium Mobilization, Inositol Phosphate Accumulation, and Protein Kinases-C Redistribution", J. Periodontol, 1998, 69(6), 642-649.
Barbasz et al., "Kininogen binding to the surfaces of macrophages", International Immunopharmacology, 2008, vol. 8, 211-216.
Mueller et al., "Macrophage Response to Peripheral Nerve Injury: The Quantitative Contribution of Resident and Hematogenous Macrophages", Laboratory Investigation, 2003, 83(2), 175-185.
Abbadie et al., Impaired neuropathic pain responses in mice lacking the chemokine receptor CCR2, PNAS, 2003, 100(13), 7947-7952.
Liu et al., "Depletion of macrophages reduces axonal degeneration and hyperalgesia following nerve injury", Pain, 2000, vol. 86, 25-32.
Mert et al., "Macrophage depletion delays progression of neuropathic pain in diabetic animals", Naunyn-Schmied Arch Pharmacol., 2009, vol. 379, 445-452.
Scott et al., "A Study of Shingles and the Development of Postherpetic Neuralgia in East London", Journal of Medical Virology, 2003, vol. 70, S24-S30.
Gauthiera et al., "Epidemiology and cost of herpes zoster and post-herpetic neuralgia in the United Kingdom", Epidemiology and Infection, 2009, 137(1), 38-47.
Smyth et al., "Prevalence of and risk factors for HIV-associated neuropathy in Melbourne, Australia 1993-2006", HIV Medicine, 2007, vol. 8, 367-373.
Hempenstall et al., "Analgesic Therapy in Postherpetic Neuralgia: A Quantitative Systematic Review", Public Library of Science-Medicine, 2005, 2(7), 628-644.
Finnerup et al., "Algorithm for neuropathic pain treatment: An evidence based proposal", Pain, 2005, vol. 118, 289-305.
Maratou et al., "Comparison of dorsal root ganglion gene expression in rat models of traumatic and HIV-associated neuropathic pain", European Journal of Pain, 2009, 13(4), 387-398.
Costigan et al., "Replicate high-density rat genome oligonucleotide microarrays reveal hundreds of regulated genes in the dorsal root ganglion after peripheral nerve injury", BMC Neuroscience, 2002, vol. 3, 18 pages.
Xiao et al., "Identification of gene expression profile of dorsal root ganglion in the rat peripheral axotomy model of neuropathic pain", Proceedings of the National Academy of Sciences, 2002, 99(12), 8360-8365.
Wallace et al., "Pharmacological, behavioural and mechanistic analysis of HIV-1 gp120 induced painful neuropathy", Pain, 2007, vol. 133, 47-63.
Wallace et al., "Characterization of rodent models of HIV-gp120 and anti-retroviral-associated neuropathic pain", Brain, 2007, vol. 130(Pt. 10), 2688-2702.
Hasnie et al., "Further characterisation of a rat model of varicella zoster virus (VZV)-associated pain", Neuroscience, 2007, 144(4), 1495-1508.
Levi et al., "Molecular cloning of a gene sequence regulated by nerve growth factor", Science, 1985, 229(4711), 393-395.
Salton et al., "VGF: A novel role for this neuronal and neuroendocrine polypeptide in the regulation of energy balance", Frontiers in Neuroendocrinology, 2000, vol. 21, 199-219.

(56) References Cited

OTHER PUBLICATIONS

Levi et al., "Processing, Distribution, and Function of VGF, a Neuronal and Endocrine Peptide Precursor", Cellular and Molecular Neurobiology, 2004, 24(4), 517-533.
Eagleson et al., "Regional differences in neurotrophin availability regulate selective expression of VGF in the developing limbic cortex", The Journal of Neuroscience, 2001, 21(23), 9315-9324.
Snyder et al., "Comparison of RPTP/beta, phosphacan, and trkB mRNA expression in the developing and adult rat nervous system and induction of RPTP/beta and phophacan mRNA following brain injury", Molecular Brain Research, 1996, vol. 40, 79-96.
Rizzi et al., "The VGF-derived peptide TLQP-21: A new modulatory peptide for inflammatory pain", Neuroscience Letters, 2008, 441(1), 129-133.
Ferri et al., "A novel neuroendocrine gene product: selective VGF8a gene expression and immuno-localisation of the VGF protein in endocrine and neuronal populations", Molecular Brain Research, 1992, vol. 13, 139-143.
Moss et al., Origins, actions and dynamic expression patterns of the neuropeptide VGF in rat peripheral and central sensory neurones following peripheral nerve injury, Molecular Pain, 2008, 4(62), 1-12.
Riedl et al., "Proteomic analysis uncovers novel actions of the neurosecretory protein VGF in nociceptive processing", The Journal of Neuroscience, 2009, 29(42), 13377-13388.
Possenti et al., "A protein induced by NGF in PC12 cells is stored in secretory vesicles and released through the regulated pathway", The EMBO Journal, 1989, 8(8), 2217-2223.
Alder et al., "Brain-derived neurotrophic factor-induced gene expression reveals novel actions of VGF in hippocampal synaptic plasticity", The Journal of Neuroscience, 2003, 23(34), 10800-10808.
Waddell et al., "Colonic eosinophilic inflammation in experimental colitis is mediated by Ly6C high CCR2 inflammatory monocyte/macrophase-derived CCL11", The Journal of Immunology, 2011, 186(10) 5993-6003.
Loetscher et al., "The ligands of CXC chemokine receptor 3, I-TAC, Mig, and IP10, are natural antagonists for CCR3", The Journal of Biological Chemistry, 2001, 276(5), 2986-2991.
Hahm et al., "Targeted deletion of the Vgf gene indicates that the encoded secretory peptide precursor plays a novel role in the regulation of energy balance", Neuron, 1999, vol. 23, 537-548.
Watson et al., "VGF ablation blocks the development of hyperinsulinemia and hyperglycemia in several mouse models of obesity", Endocrinology, 2005, 146(2), 5151-5163.
Bridges et al., "The synthetic cannabinoid WIN55,212-2 attenuates hyperalgesia and allodynia in a rat model of neuropathic pain", British Journal of Pharmacology, 2001, vol. 133, 586-594.
Kim et al., "An experimental model for peripheral neuropathy produced by segmental spinal nerve ligation in the rat", Pain, 1992, vol. 50, 355-363.
Fleetwood-Walker et al., "Behavioural changes in the rat following infection with varicella-zoster virus", Journal of General Virology, 1999, vol. 80, 2433-2436.
"Treating I definition of treating by Medical dictionary," The American Heritage® Medical Dictionary (2007), retrieved Aug. 29, 2016 from http://medical-dictionary.thefreedictionary.com/treating. pp. 1-2.
Zang et al., "Selection and application of peptide-binding peptides," Nat Biotechnol. 18(1):71-4 (Jan. 2000).

Figure 3A & B
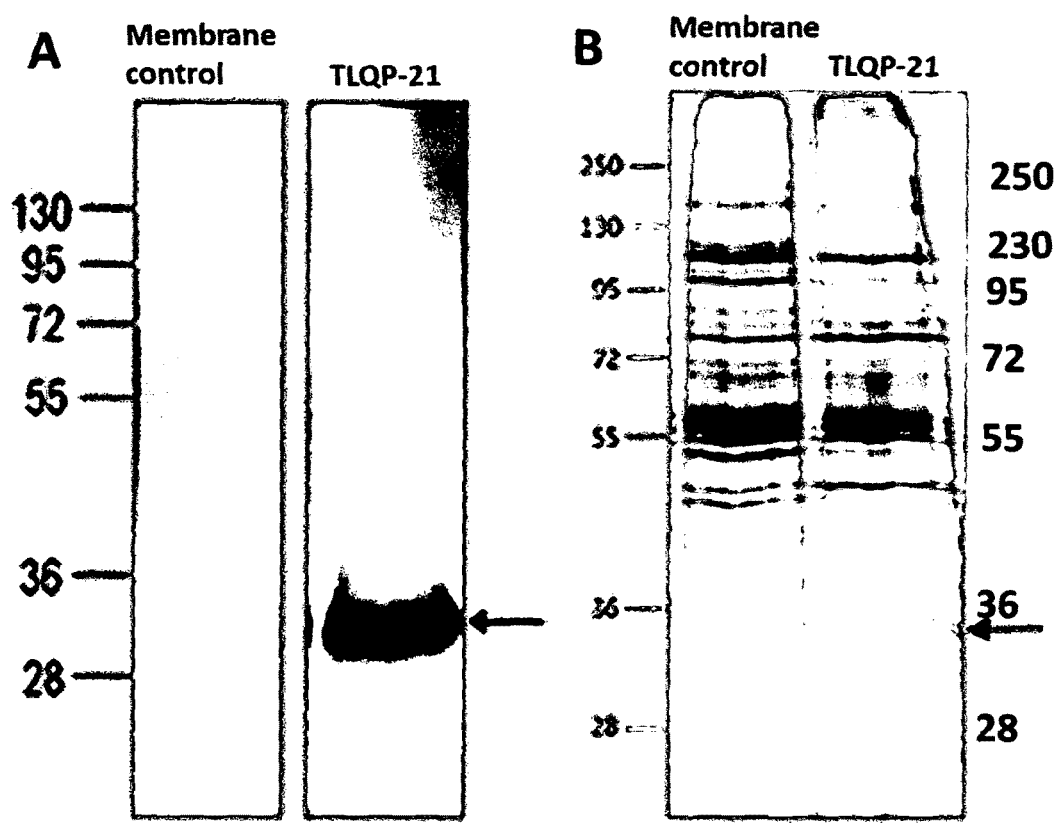

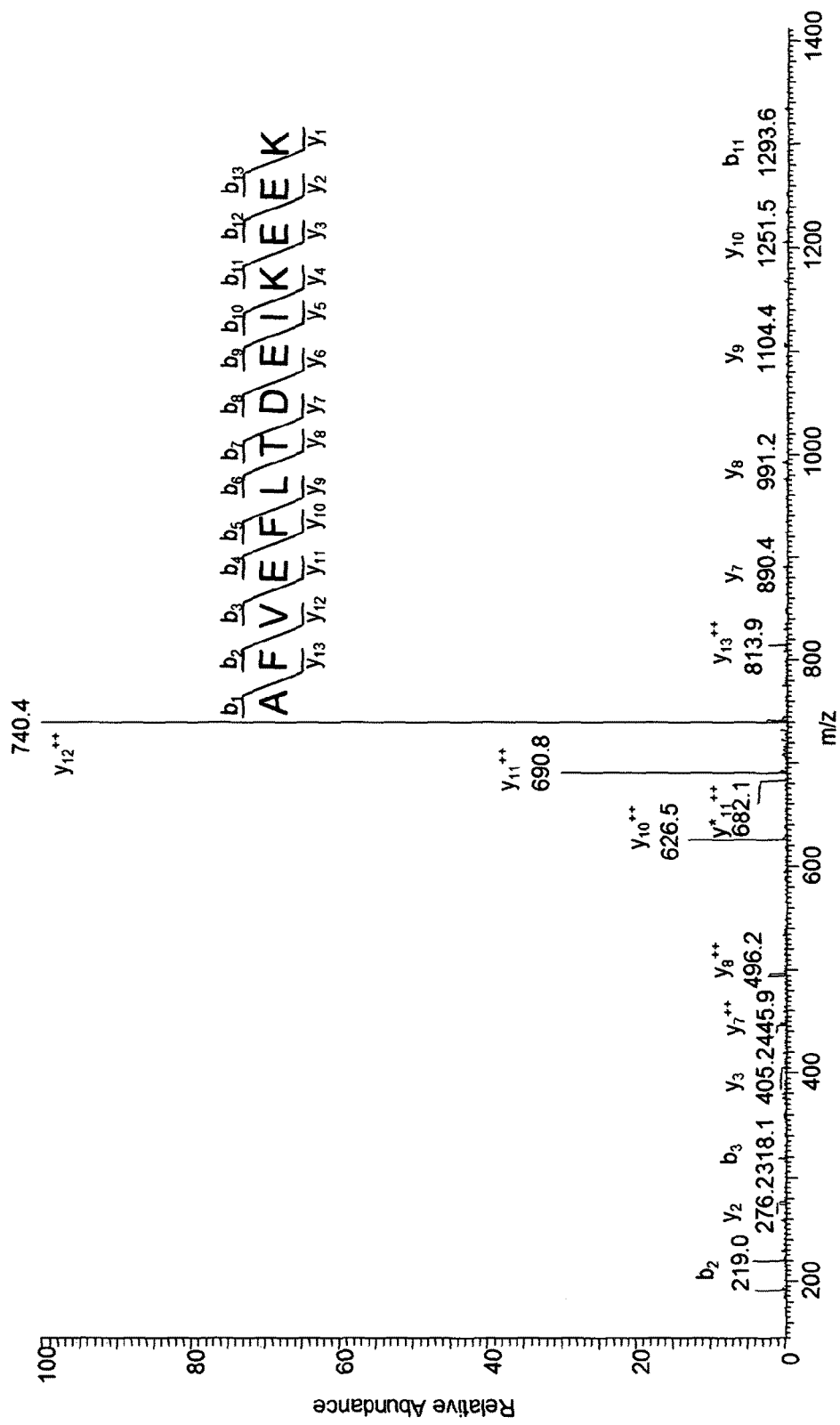

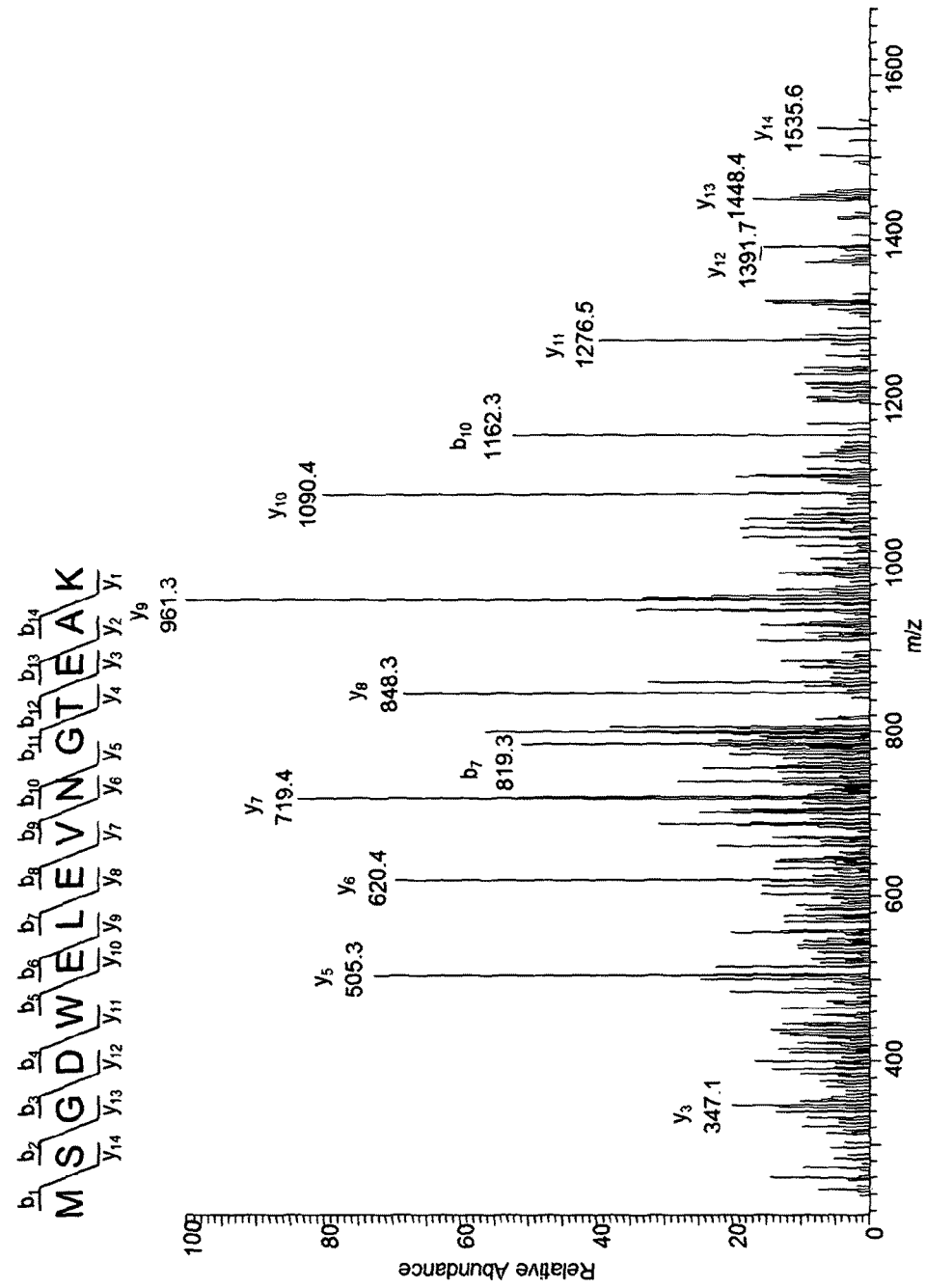
Figure 3C(b) Mass Spectrum for peptide MSGDWELEVNGTEAK

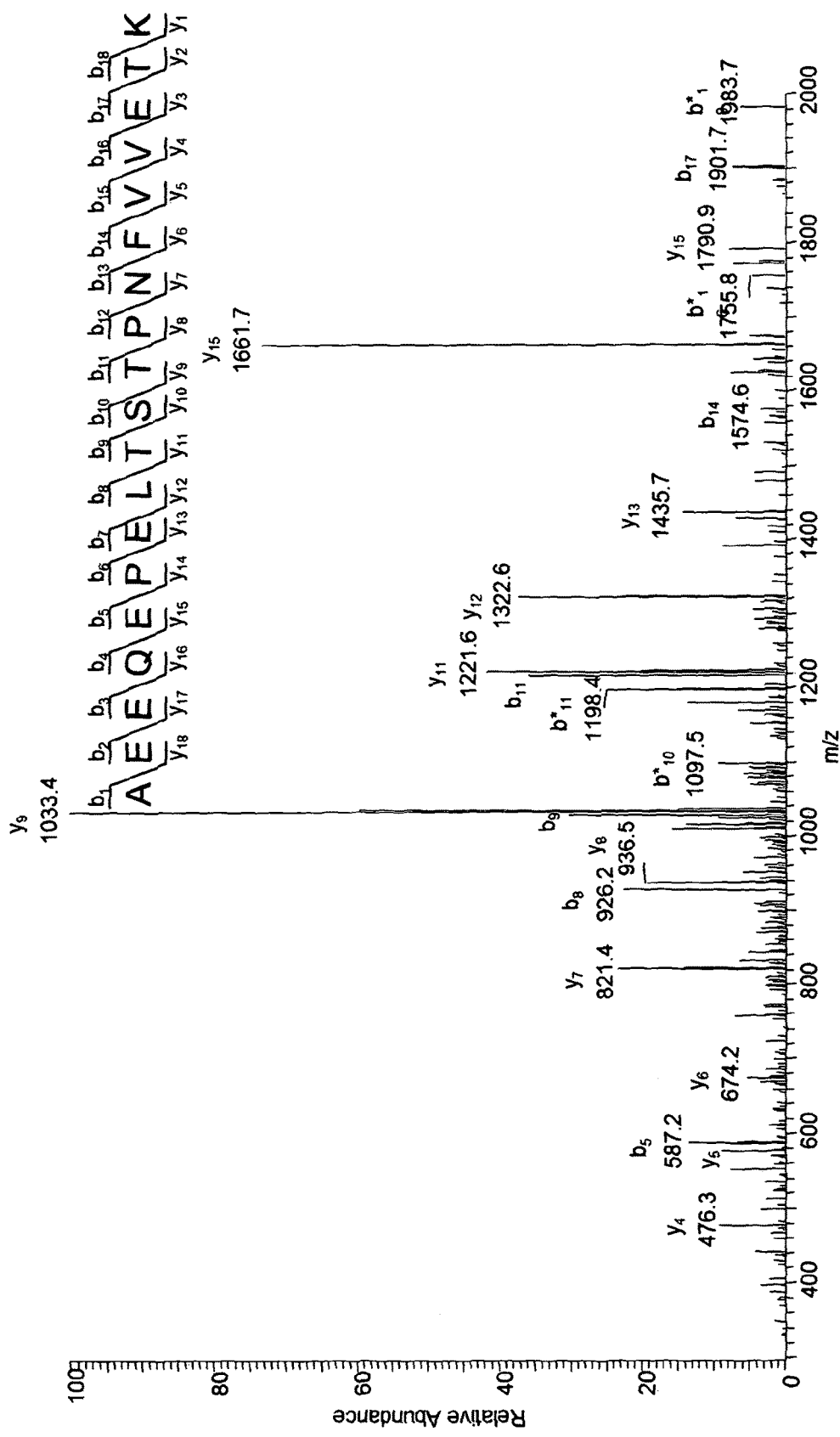
Figure 3C(c) Mass Spectrum for peptide AEEQEPELTSTPNFVVETK

Figure 3D, E & F
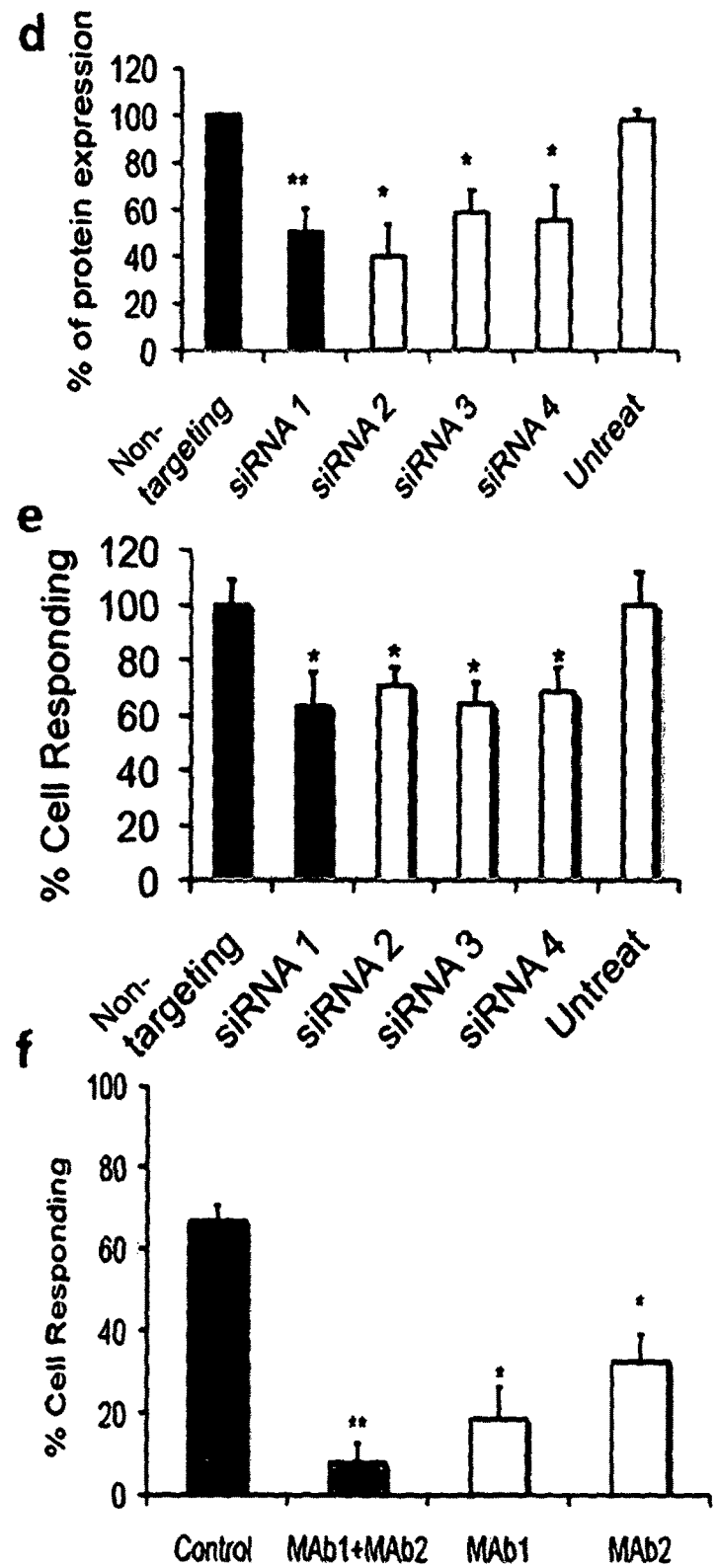

Figure 7A & B
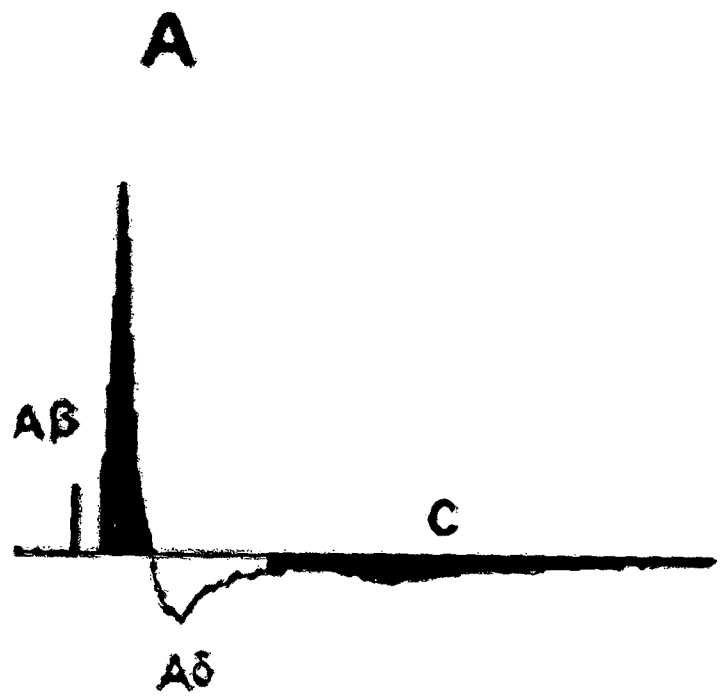
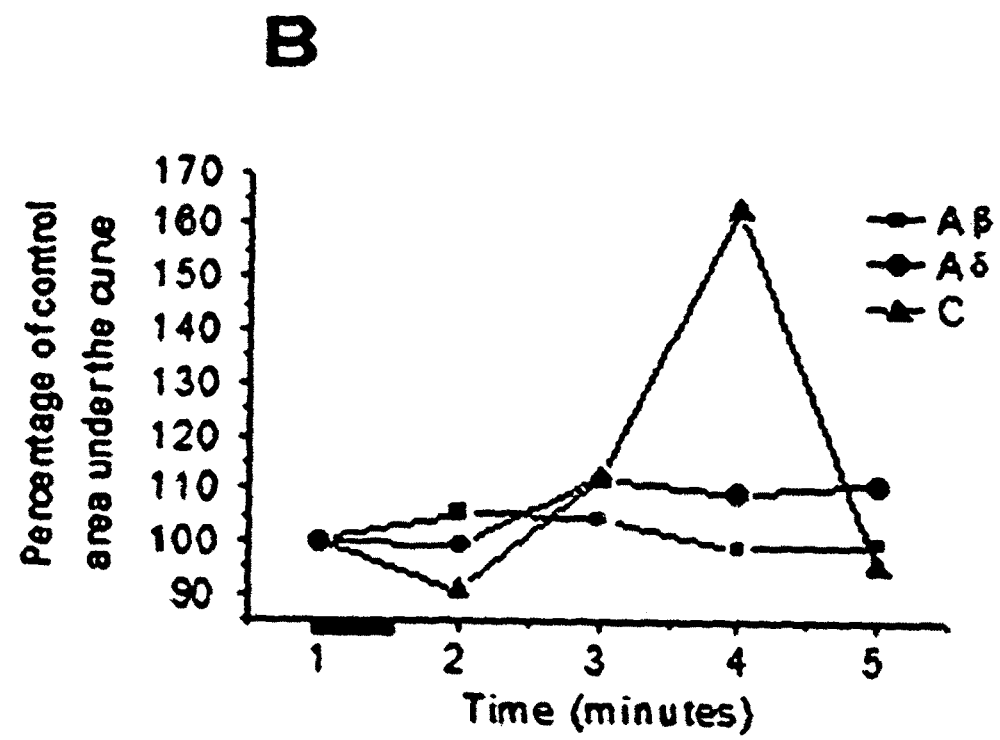

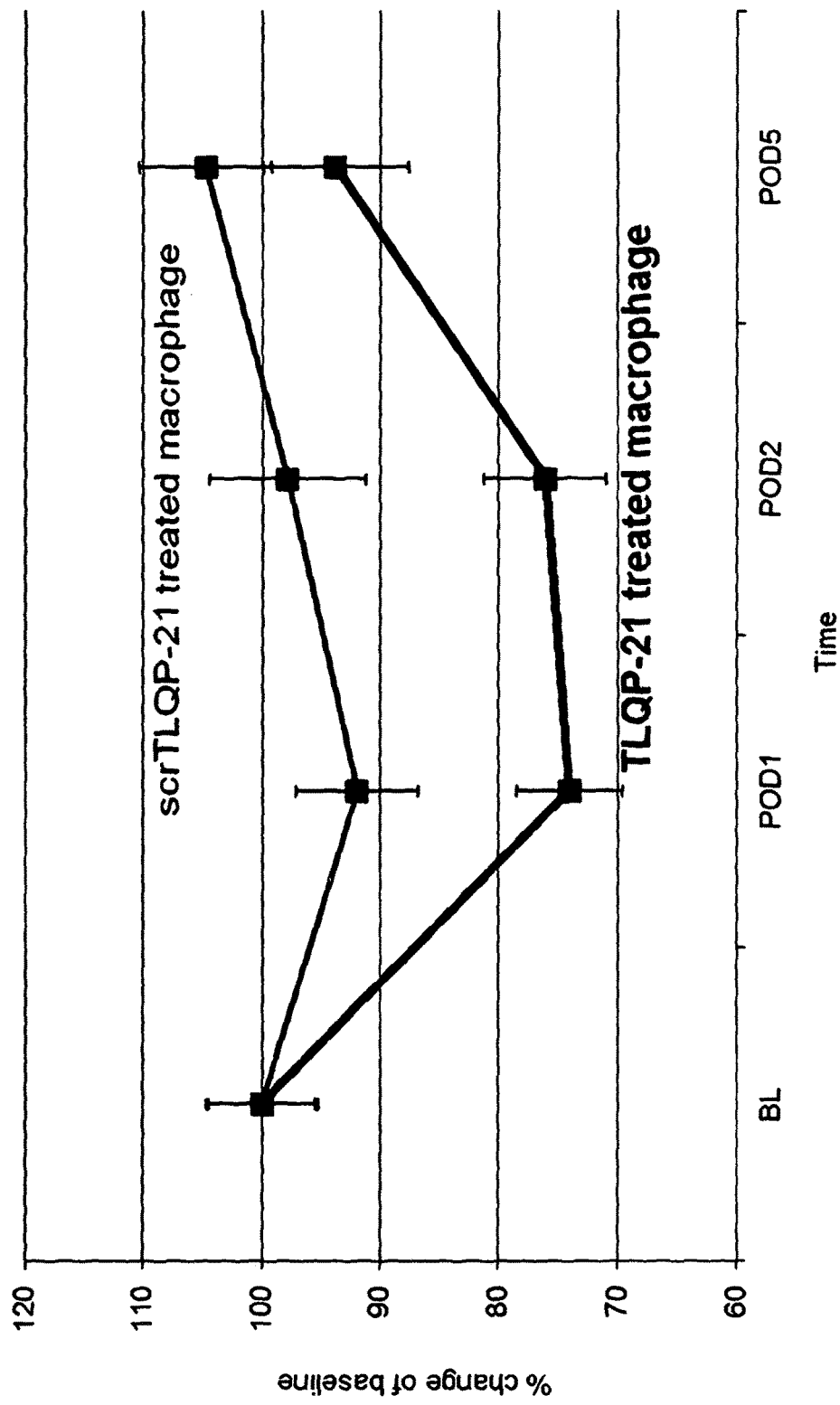
Figure 8 Hind paw injection of TLQP-21-treated macrophage produced tactile allodynia.

METHODS OF TREATING PAIN BY INHIBITION OF VGF ACTIVITY

CROSS REFERENCE TO RELATED APPLICATIONS

This application is a US national phase of International Application No. PCT/GB2013/050162 filed on Jan. 25, 2013, which claims priority to Great Britain Patent Application No. 1201332.2 filed on Jan. 26, 2012. The entire disclosure contents of each of these applications are hereby incorporated by reference into the present application.

The present disclosure relates to methods of treating neuropathic pain comprising administering an inhibitor of VGF activity, in particular inhibiting or blocking activity in the form of signaling resulting from the binding of VGF or a peptide thereof and the receptor gC1qR, and methods of screening for said inhibitors.

Neuropathic pain describes a chronic, usually disabling, type of pain which is generally refractive to treatment. The prevalence of some of the major diseases which result in the development of neuropathic pain conditions is increasing and the individual and societal costs resulting from the incidence of neuropathic pain conditions is very substantial. For example, about 10-20% of acute herpes zoster patients progress to the serious complication of postherpetic neuralgia, a neuropathic pain condition[1,2]. Again, in the developed world, about 40% of ambulatory HIV patients suffer from neuropathic pain conditions, which remain undiminished by the existing drug therapy for this disease[3].

Treatment options for neuropathic pain conditions are limited and have a poor success rate[4,5]. A major reason for the failure to develop effective drug therapy for neuropathic pain has been the difficulty of distinguishing targets which are causative in the development or maintenance of neuropathic pain from those which are merely associated with related nerve injury and regeneration.

The present inventors have searched for similarities in gene expression between aetiologically disparate models of neuropathic pain[6]. They have compared dorsal root ganglion (DRG) gene expression profiles in rat models of traumatic nerve injury, and HIV-related, peripheral neuropathic pain conditions, respectively[6]. Although about 2700 genes were found to be dysregulated in each of the individual models, they found that only 14 and 25 genes or expressed sequence tags (ESTs) were commonly up-regulated and down-regulated, respectively, in both models. Further comparison with unpublished microarray data from a model of varicella zoster infection revealed that only three up-regulated genes are common to all three neuropathic pain models. While two of these genes were ESTs, the third was vgf, which was confirmed by qRT-PCR.

Whilst there have been publications in the art in relation expression patterns of the neuropeptide VGF in rat peripheral and central sensory neurones following peripheral nerve injury we don't believe that any one in the art to date has appreciated that VGF is a common factor in all clinical neuropathic pain conditions.

This insight is very significant because it allows treatments for neuropathic pain to be developed that work across the broad spectrum of conditions that exhibit neuropathic pain. This is important because it means that an effective treatment is more likely to developed and brought forward into the clinic because the disease target profile is significantly simplified as each sub-category of associated diseases does not need to be treated separately.

The present inventors believe that VGF is an ideal target of the treatment of neuropathic pain, regardless of the underlying source of the pain. It appears that VGF is a multifunctional a pivotal molecule in the sensory nervous system in the generation and maintenance of neuropathic pain.

Furthermore the present inventors have established a novel pain signaling pathway from the binding of VGF or a peptide thereof of the type TLQP-21 with the receptor gC1qR, which is specifically implicated in a neuropathic pain signaling pathway. Targeting this pathway with an inhibitor in a specific manner may be advantageous in that it may minimise off target effects.

SUMMARY OF THE DISCLOSURE

Thus the present disclosure provides a method of treating a patient with neuropathic pain by administering a therapeutically effective amount of an inhibitor of VGF activity.

The present inventors have also established that the VGF activity associated with neuropathic pain may be mediated by binding of peptides of VGF to a receptor gC1qR. This is important because it provides a mechanism for therapeutic intervention and a new therapeutic target for neuropathic pain namely gC1qR.

Thus in one aspect there is provide a method of treating a patient with neuropathic path comprising administering a therapeutically effective amount of an inhibitor of the interaction between VGF or a peptide of the type TLQP-21 and the receptor gC1qR.

In one embodiment the gC1qR receptor is on the surface of macrophages, such as microglia.

Also provided is use of an inhibitor of the interaction between VGF or a peptide of the type TLQP-21 and the receptor gC1qR in the manufacture of a medicament for the treatment of pain, in particular neuropathic pain.

In one embodiment there is provided an inhibitor specific to the receptor gC1qR which inhibits binding of the receptor to VGF or a peptide of the type TLQP-21 and/or inhibits the biological signally generated by said binding, for use in treatment, in particular in the treatment of pain, particularly neuropathic pain.

In one embodiment there is provide use of an inhibitor specific to the receptor gC1qR which inhibits binding of the receptor to VGF or a peptide of the type TLQP-21 and/or inhibits the biological signally generated by said binding, for the manufacture of a medicament for the treatment of pain, particularly neuropathic pain.

In one embodiment there is provided an inhibitor specific to VGF or a peptide thereof, for example of the type TLQP-21 which inhibits binding of the receptor gC1qR to VGF or a peptide of the type TLQP-21 and/or inhibits the biological signally generated by said binding, for use in treatment, in particular in the treatment of pain, particularly neuropathic pain.

In a further embodiment there is provided assays for identifying a suitable inhibitor wherein the assay is based on blocking the binding and/or signaling between VGF or a peptide thereof of the type TLQP-21 and the receptor gC1qR.

Also provided are inhibitors identified or obtainable from said method.

DETAILED DESCRIPTION OF THE DISCLOSURE gC1q-R as employed herein refers to the receptor with the UniProt number Q9NPY3.

VGF (non-acronymic) was originally identified in PC12 cells[12]. The vgf gene encodes a neuropeptide precursor with a restricted pattern of expression in neurons in the central/peripheral nervous systems and certain endocrine cells, which is highly conserved between rodents and man[13]. The expression of VGF is inducible by neurotrophins in various cells[12,14,15] and VGF-expressing cells also express cognate neurotrophin receptors[16]. In the somatosensory system, small diameter neurons of DRG[17] and fibres in the superficial spinal dorsal horn and spinal lamina X[18] express VGF, which predicts that these neurons are NGF sensitive and of a nociceptor phenotype[17,18].

Human VGF is registered in UniProt under the reference O15240. The signal peptide is amino acids 1-22. The neurosecretory protein VGF is amino acids 23-615. Neuroendocrine regulatory peptide-1 (NERP-1) is amino acids 281-306 and neuroendocrine regulatory peptide-2 (NERP-2) is amino acids 310-347.

VGF undergoes endoproteolytic cleavage and the products are released from secretory granules in dense core vesicles on depolarisation[21]. Several VGF-derived peptides have been identified, which are named by the first 4 amino acids and their overall length[14]. VGF-derived peptides are involved in a number of processes, including enhancement of synaptic activity and plasticity[7,22].

Functional roles of VGF-derived peptides in pain pathways have also been identified. Intrathecal application of TLQP-62 (SEQ ID NO: 1) to rats results in a long-lasting mechanical and cold behavioural allodynia[19]. Application of the same peptide to spinal cord slices also leads to an increase in the frequency of spontaneous excitatory post synaptic currents[19].

Another peptide, LQEQ-19 (SEQ ID NO: 2) induces p38 MAP kinase phosphorylation in spinal microglia and in the BV-2 microglial cell line[20].

VGF as employed herein is intended to include the full length secreted protein and active fragments thereof, including peptide TLQP-62 (SEQ ID NO: 1), LQEQ-19 (SEQ ID NO: 2) and TLQP-21 (SEQ ID NO: 3) which is amino acids 556-576 of the precursor molecule, NERP-1 and NERP-2.

VGF activity as employed herein is the biological activity of the protein or an active fragment thereof, in particular the VGF activity associated with pain mechanisms in vivo, and especially the activity associated with the signaling pathways involved in neuropathic pain, and especially as mediated through the receptor gC1Qr.

Inhibition of VGF activity as employed herein includes inhibition of expression of the protein, for example using an oligonucleotide such as RNAi technology or other routine techniques employed for reducing gene expression. There are a variety of ways that oligonucleotides can be used to reduce expression of a target endogenous gene, see for example US2008/050342.

Inhibition of VGF activity also includes the use of antibodies or binding fragments thereof, for example neutralising antibodies directed to the protein or active fragments thereof. Neutralising antibody as employed herein is one that reduces or eliminates a targeted biological activity by any relevant mechanism including blocking, agonising or anta-antagonising.

The term "inhibition of VGF activity" also extends to inhibition of VGF activity by interfering with a signally pathway involved in the activation of or sustaining VGF activity. At the time writing MEK was known be involved in VGF survival in vivo.

In one embodiment inhibition of VGF activity refers to the activity of VGF associated with stimulating pain signaling pathways, in particular neuropathic pain signaling pathways, such as the activity resulting from binding of VGF or a peptide thereof of the TLQP-21 type to the receptor gC1qR. This activity can be inhibited by targeting VGF or a relevant peptide thereof or by targeting the receptor gC1qR.

The present inventors have shown herein that TLQP-21 binds to the receptor gC1qR. In one embodiment the VGF activity specifically refers to inhibiting or blocking signaling resulting from this interaction or a corresponding interaction.

A corresponding interaction as employed herein refers to VGF or a peptide binding to the receptor gC1qR in the same way as TLQP-21, in particular a binding contact that engages some or all of the same amino acid residues on gC1qR as TLQP-21 binding.

A peptide of the TLQP-21 type as employed herein is a one which has a corresponding interaction with the receptor gC1qR.

In one embodiment the inhibitor is an antibody, for example an anti-VGF antibody. An anti-VGF antibody as employed herein is intended to refer to an antibody that is specific to VGF or an active/binding fragment thereof, in particular specific to TLQP-21.

In one embodiment the inhibitor is an anti-gC1qR antibody. An anti-gC1qR antibody as employed herein is intended to refer to an antibody that is specific to gC1qR or an active/binding fragment thereof.

In one embodiment an antibody or binding fragment thereof targets an epitope on VGF or gC1qR that physically prevents the binding or the interaction of VGF or a peptide thereof of the TLQP-21 type with the receptor gC1qR.

In one embodiment an antibody or binding fragment thereof targets an epitope on VGF or gC1qR that causes a conformational change in the protein and prevents the binding and/or signally generated by VGF or a peptide thereof of the TLQP-21 type with the receptor gC1qR.

Specific as employed herein is intended to refer to the fact the antibody selectively binds the target protein and has no affinity or significantly lower affinity for other proteins.

Antibodies generated against polypeptides may be obtained, where immunisation of an animal is necessary, by administering the polypeptides to an animal, in particular a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as camelids, rabbits, mice, rats, sheep, cows or pigs may be immunized. However, mice, rabbits, pigs and rats are generally employed.

Antibodies for use in the present invention include whole antibodies and functionally active fragments or derivatives thereof and may be, but are not limited to, polyclonal, monoclonal, multi-valent, multi-specific such as bispecific, humanized or chimeric antibodies, single chain antibodies, Fab fragments, Fab' and F(ab')2 fragments, fragments produced by a Fab expression library, anti-idiotypic (anti-Id) antibodies, and epitope-binding fragments of any of the above including nanobodies and diabodies.

Particular antibody fragments also include those described in WO 2005/003169, WO 2005/003170 and WO 2005/003171.

Antibody fragments and methods of producing them are well known in the art, see for example Verma et al., 1998, Journal of Immunological Methods, 216, 165-181. Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule. The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgGl and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

Variants of these constant region domains may also be used. For example IgG molecules in which the serine at position 241 has been changed to proline as described in Angal et al., Molecular Immunology, 1993, 30 (1), 105-108. Particularly suitable is the IgG4 constant domain comprising this change.

Monoclonal antibodies may be prepared by any method known in the art such as the hybridoma technique (Kohler & Milstein, 1975, Nature, 256:495-497), the trioma technique, the human B-cell hybridoma technique (Kozbor et al, 1983, Immunology Today, 4:72) and the EBV-hybridoma technique (Cole et al, Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al, 1996, Proc. Natl. Acad. Sci. USA 93(15): 7843-78481; WO 92/02551; WO 2004/051268 and WO 2004/106377.

Humanized antibodies are antibody molecules from non-human species having one or more complementary determining regions (CDRs) from the non-human species and a framework region from a human immunoglobulin molecule (see, e.g. U.S. Pat. No. 5,585,089; WO 91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic.

Bivalent antibodies may be made by methods known in the art (Milstein et al., 1983, Nature 305:537-539; WO 93/08829, Traunecker et al, 1991, EMBO J. 10:3655-3659).

Multi-valent antibodies may comprise multiple specificities or may be monospecific (see for example WO 92/22853).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al (Eur. J. Immunol. 1994, 24:952-958), Persic et al (Gene, 1997 187 9-18), Burton et al (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Techniques for the production of single chain antibodies, such as those described in U.S. Pat. No. 4,946,778 can also be adapted to produce single chain antibodies to VGF. Also, transgenic mice, or other organisms, including other mammals, may be used to express human antibodies.

A polyclonal anti-VGF antibody is available from Abcam under the number ab69989 and from Novus under the number NBP1-01050. An anti-VGF antibody is available from Sigma-Aldrich under the number PRS4611. An anti-VGF antibody is available from antibodies online under the number ABIN460896.

In one embodiment the present disclosure relates to use of a known anti-VGF antibody in the treatment of neuropathic pain.

Antibodies to gC1qR include rabbit and mouse antibodies from LifeSpan BioSciences Inc LS-B3069, LS-B7064, LS-7311, LS-C154592, LS-C154702, LS-C97452, LS-C79452, LS-C97453, LS-C139946, LS-C34554 and LS-C34555. Antibodies such as these can be employed to prepare chimeric or humanised antibodies.

In one embodiment the inhibitor is a peptide that binds to the target, for example gC1qR or VGF (or an active fragment thereof which binds the receptor gC1qR). However, after the briding the peptide inhibitor fails to generate a relevant biological signal and due to the competitive nature of the binding kinetic minimises the opportunity for genuine binding of the VGF and the receptor. In one embodiment the peptide inhibitor has a similar or identical to a portion of the receptor gC1qR. In one embodiment the peptide inhibitor is a mutated from of VGF or a fragment such as TLQP-21 wherein the mutation enables the peptide to bind but not to induce biological signaling.

In one embodiment a MEK inhibitor is employed in the methods of the present disclosure.

Examples of MEK inhibitors are disclosed in WO2011/156588, WO2010/121646, WO2010/179124, WO2009/093013, WO2009/093009, WO2009/264411, WO2007/044084, WO2003/077914 and US2010/197676 wherein the compounds of each of the same are incorporated herein by reference. In one embodiment the MEK inhibitor is PD 98059:

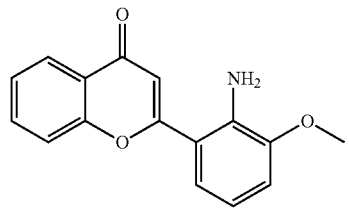 [SMILES: COc1cccc(-c2cc(=O)c3ccccc3o2)c1N]

In one embodiment there is provided an inhibitor according to the present disclosure for use in the manufacture of a medicament for treatment of pain, for example neuropathic pain, particularly as described herein.

In one embodiment there is provided an inhibitor according to the present disclosure for use in treatment, for example in the treatment of pain, in particular neuropathic pain.

Neuropathic pain as employed herein is intended to refer to central or peripheral neuropathic pain, which includes neuropathic pain selected from the group comprising neuropathic pain associated with nerve injury or damage, postherpetic neuropathy, neuropathic pain associated with HIV/AIDS, neuropathic pain associated with diabetic neuropathy, neuropathic pain associated with fibromyalgia, neuropathic pain associated with alcohol neuropathy, neuropathic pain associated with an amputation, neuropathic pain associated with facial nerve problems such as Bell's Palsy, neuropathic pain associated with cancer including chemotherapy and neuropathic pain associated with multiple sclerosis.

In one embodiment the neuropathic pain is associated with nerve injury or damage, postherpetic neuropathy (such as following varicella zoster infection) and neuropathic pain associated with HIV/AIDS.

Other causes of neuropathic pain include: chemokine or drug induced neuropathy including for example chemotherapy; radiation injury; surgery; cancer for example from compression of a nerve by a tumor; diabetes; certain strokes; and excessive inflammatory responses, for example that result in tissue damage.

Chronic pain may also be associated with syndromes such as post-traumatic stress syndrome.

In one embodiment the neuropathic pain is nociceptive pain, that is pain which is often described as aching. In one embodiment the neuropathic pain is produced by stimuli which are normally considered non-painful (allodynia). In one embodiment the neuropathic pain is continuous. In one embodiment the neuropathic pain in episodic. In one embodiment the neuropathic pain is peripheral. In one embodiment the neuropathic pain is central. In one embodiment the patient is a human.

In one embodiment the entity employed in the method of the present disclosure is a direct VGF inhibitor.

A direct VGF inhibitor as employed herein is intended to refer to a compound, molecule, protein, antibody or similar that works directly on VGF protein or an active fragment thereof, or the gene encoding VGF or a gene transcript such as mRNA. This embodiment would not include indirect inhibition, for example employing a MEK inhibitor.

The present disclosure relates to an inhibitor of VGF activity, as described herein in therapy, for example for the treatment of pain, such as neuropathic pain, such as described above.

In one embodiment the entity employed in the method of the present disclosure is a direct gC1qR inhibitor.

A direct gC1qR inhibitor as employed herein is intended to refer to a compound, molecule, protein, antibody or similar that works directly on gC1qR protein or an active fragment thereof, or the gene encoding the receptor or a gene transcript such as mRNA.

In an independent aspect the present disclosure relates to a method of treating Fibromyalgia comprising administering a therapeutically effective amount of an inhibitor of VGF activity, as described herein. Fibromyalgia is a complicated and little understood illness with a variety of symptoms in addition to neuropathic pain. These symptoms may include fatigue, difficulty with cognitive functions (including ADHD), modulation of appetite which may be associated with weight gain etc. The treatment of the present disclosure may be useful in ameliorating or eliminating one or more of these symptoms.

The inhibitor employed in the present disclosure may be employed with other active agents, for example an analgesic, steroid, anti-epileptic such as pre-gablin and gabapentin, a beta-blocker such as S-pindolol or similar.

The inhibitor employed in the methods of the present disclosure may be administered in any suitable form, for example topical including by inhalation therapy, oral and parentheral, as appropriate to the selected inhibitor.

Generally antibodies according the disclosure will be introduced in a formulation for injection or infusion. Suitable formulations may be best used in the form of a sterile aqueous solution which may contain other substances, for example enough salts or saccharides, in particular a monosaccharide, to make the solution isotonic with blood. Examples of parenteral administration include one or more of: intravenously, intraarterially, intraperitoneally, intrathecally, intraventricularly, intraurethrally, intrasternally, intracranially, intramuscularly or subcutaneously administering the agent, and/or by using infusion techniques.

In one embodiment the formulation is adapted for delivery by infusion or slow injection.

In one embodiment the formulation is adapted for delivery by bolus injection.

Preservatives and/or stabilisers may be provided in the pharmaceutical composition. Examples of preservatives include sodium benzoate, sorbic acid and esters of p-hydroxybenzoic acid. Antioxidants and suspending agents may be also used.

For some embodiments, the agents employed in the method the disclosure may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e. g. as a carrier, diluent or solubiliser. Alpha-, beta- and gamma-cyclodextrins are most commonly used and suitable examples are described in WO 91/11172, WO 94/02518 and WO 98/55148.

Compounds, such as MEK inhibitors employed in the methods of the present disclosure may be amenable to oral administration including buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin or HPMC (hydroxypropyl methylcellulose) capsules. Preferred excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules, may be filled with a powder (of medicament alone or as blend with selected filler(s)) or alternatively a liquid, each comprising one or more inhibitors according the present disclosure and a carrier. Where the capsule is filled with a powder the inhibitor and/or the carrier may be milled or micronised to provide material with an appropriate particle size.

Formulations employed in the present disclosure may be coated, for example with as an enteric coating when administered orally as a tablet or capsule. The tablet or capsule, as appropriate, may, for example be coated by a thin film such as a EUDRAGIT® film available from Rohm Pharma Polymers, which allows controlled dissolution in the gastrointestinal tract. The films are available as cationic polymers such as EUDRAGIT® E 100 (aminoalkyl methacylate copolymers) or as anionic acrylic polymers such as EUDRAGIT® L (methacrylic acid copolymers) and EUDRAGIT S.

Permeable acrylic polymers such as EUDRAGIT® RL (amino methacrylate copolymer) and EUDRAGIT® RS are also available.

Typically, a physician will determine the actual dosage which will be most suitable for an individual subject. The specific dose level and frequency of dosage for any particular individual may be varied and will depend upon a variety of factors including the activity of the specific salt employed, the metabolic stability and length of action of that salt, the age, body weight, general health, sex, diet, mode and time of administration, rate of excretion, drug combination, the severity of the particular condition, and the individual undergoing therapy.

For administration to humans, the daily dosage level of the agent may be in single or divided doses. For systemic administration the daily dose as employed for adult human treatment it will range from 0.1-100 mg/Kg body weight, such as 5-60 mg/Kg body weight, which may be administered in 1 to 4 daily doses, for example, depending on the route of administration and the condition of the patient. When the composition comprises dosage units, each unit will preferably contain 100 mg to 1 g of active ingredient. The duration of treatment will be dictated by the rate of response rather than by arbitrary numbers of days.

In one embodiment the treatment regime is continued for 1, 2, 3, 4, 5, 6, 7, 8, 9, 10, 11, 12, 13, 14, 15, 16, 17, 18, 19, 20, 21 or more days.

Paragraph 1. Also provided is an in vitro method of screening for an inhibitor of VGF activity comprising the steps of: running an assay to determine the strength of competitive and/or non-competitive binding of a potential inhibitor to the receptor gC1qR, and selecting inhibitors showing affinity for the receptor gC1qR.

Paragraph 2. In one embodiment there is provided a method according to paragraph 1 further comprising the step of: running an assay to determine the inhibition of binding of VGF to the receptor gC1qR by the potential inhibitor.

Paragraph 3. In one embodiment there is provided a method according to paragraph 1 or 2 comprising the step of: running an assay to determine the inhibition of binding of any peptide derived from the entire peptide sequence encoded by the vgf gene to the receptor gC1qR by the potential inhibitor.

Paragraph 4. In one embodiment there is provided a method according to paragraph 3 comprising the step of: running an assay to determine the inhibition of binding of TLQP-21 to the receptor gC1qR by the potential inhibitor.

The method according to paragraphs 1 to 4 may also or alternatively be based on detecting the inhibition of biological signaling after the binding of VGF or a peptide of the type TLQP-21 to the receptor gC1qR.

Paragraph 5. In one embodiment there is provided method according to any one of paragraphs 1 to 4 wherein the inhibitor is an antibody or binding fragment thereof, such as an antibody.

Paragraph 6. In one embodiment there is provided method according to any one of claims 1 to 4, wherein the inhibitor is a peptide or polypeptide.

Paragraph 7. In one embodiment there is provided a method according to any one of claims 1 to 4, wherein the inhibitor is a chemical agent.

Paragraph 8. In one embodiment there is provided a method according to any of the preceding numbered paragraphs for identifying an inhibitor useful in therapy, preferably for the treatment of pain, for example, wherein the pain is neuropathic pain, preferably selected from the group comprising neuropathic pain associated with nerve injury or damage, postherpetic neuropathy, neuropathic pain associated with HIV/AIDS, neuropathic pain associated with diabetic neuropathy, neuropathic pain associated with fibromyalgia, neuropathic pain associated with alcohol neuropathy, neuropathic pain associated with an amputation, neuropathic pain associated with facial nerve problems such as Bell's Palsy, neuropathic pain associated with cancer and neuropathic pain associated with multiple sclerosis.

Paragraph 9. Also provided is an in vitro method of screening for an inhibitor of VGF mediated activity for use in the treatment of pain, in particular neuropathic pain, comprising the step of measuring the modulation (such as inhibition) of signaling through the receptor gC1q-R or binding thereto by a test agent, for example where the method comprises determining if the agent binds the receptor gC1q-R.

Paragraph 10. In one embodiment there is provided an inhibitor of the receptor gC1q-R identified by the method of any one of paragraphs 1 to 9.

Paragraph 11. In one embodiment there is provided an inhibitor according to paragraph 10 for use in treatment, preferably for the treatment of pain, in particular for use in the treatment of neuropathic pain, for example wherein the neuropathic pain is selected from the group comprising neuropathic pain associated with nerve injury or damage, postherpetic neuropathy, neuropathic pain associated with HIV/AIDS, neuropathic pain associated with diabetic neuropathy, neuropathic pain associated with fibromyalgia, neuropathic pain associated with alcohol neuropathy, neuropathic pain associated with an amputation, neuropathic pain associated with facial nerve problems such as Bell's Palsy, neuropathic pain associated with cancer and neuropathic pain associated with multiple sclerosis.

Paragraph 12. There is also provided an anti-gC1q-R antibody for use in treatment, for example treatment of pain, preferably in the treatment of neuropathic pain, in particular wherein the antibody blocks binding of any peptide derived from the entire peptide sequence encoded by the vgf gene to the receptor gC1q-R.

Paragraph 13. An anti-gC1q-R antibody according to paragraph 11, wherein the antibody is specific to gC1q-R.

Paragraph 14. In one embodiment the anti-gC1q-R antibody is a neutralising antibody.

Paragraph 15. A method of treating a patient with neuropathic pain by administering a therapeutically effective amount of an inhibitor of VGF activity which prevents signal through or binding to the receptor gC1q-R.

In one embodiment there is provide an inhibitor of VGF activity mediated through the gC1q-R for use in treatment, for example, for use in the treatment of neuropathic pain, in particular wherein the neuropathic pain is selected from the group comprising neuropathic pain associated with nerve injury or damage, postherpetic neuropathy, neuropathic pain associated with HIV/AIDS, neuropathic pain associated with diabetic neuropathy, neuropathic pain associated with fibromyalgia, neuropathic pain associated with alcohol neuropathy, neuropathic pain associated with an amputation, neuropathic pain associated with facial nerve problems such as Bell's Palsy, neuropathic pain associated with cancer and neuropathic pain associated with multiple sclerosis.

Examples of suitable inhibitors of VGF activity include wherein the inhibitor is an antibody or fragments thereof specific to VGF or specific to the receptor gC1qR.

In one embodiment there is provided use of an anti-gC1q-R antibody in the manufacture of a medicament for use in treatment, of pain, preferably in the treatment of neuropathic pain in particular as defined herein.

In one embodiment there is provided an anti-body specific to SEQ ID NO: 3 (TLQP-21), for use in treatment, preferably in the treatment of pain, such as neuropathic pain in particular as described herein, for example wherein the antibody in neutralising, such as inhibiting binding of the peptide to gC1q-R and/or inhibits signally of the induced by binding of the peptide to gC1q-R.

Also provided is use of TLQP-21 in screening for an inhibitor of VGF activity.

In one embodiment there is provided use of the receptor gC1q-R or a functionally active fragment thereof in screening for an inhibitor of VGF activity.

In one embodiment there is provided use of a combination of a VGF peptide such as TLQP-21 and the receptor gC1q-R or a functionally active fragment thereof in screening for an inhibitor of VGF activity.

In one embodiment there is provided an inhibitor identified or obtainable from the screening method described herein.

In one embodiment there is provide a kit comprising the components required for an assay described herein, for example purified gC1qR or an active fragment thereof and/or VGF or a peptide of the type TLQP-21, and optionally comprising an reporter system.

In the context of this specification "comprising" is to be interpreted as "including".

Aspects of the invention comprising certain elements are also intended to extend to alternative embodiments "consisting" or "consisting essentially" of the relevant elements.

Example

BRIEF DESCRIPTION OF THE FIGURES

FIG. 3A-F gC1qR is the receptor for TLQP-21. a, Biotinylated TLQP-21 was conjugated to Sulfo-EMCS cross-linker, and applied to membrane fractions of 6 weeks old rat brain and spinal cord for cross-linking (boric acid buffer, pH 8, with 150 mM NaCl, 3 hours incubation on ice). The reaction was terminated using 50 mM Tris buffer, and samples were ethanol precipitated and resolved using Tricine-PAGE and visualised by Western blot analysis by streptavidin-horse radish peroxidase. A clear band at ~30 kDa (indicated by an arrow) was observed following chemical crosslinking using biotinylated TLQP-21., which was many orders of magnitude greater than the corresponding band in the membrane control lane using unconjugated Sulfo-EMCS cross-linker. b, Membrane fractions of P4 rat brain was applied to either monomeric avidin column attached with TLQP-21 or monomeric avidin column only ("Negative control"). Following considerable washes, proteins bound to the columns were eluted and resolved on SDS-PAGE, followed by silver staining. A ~30 kDa band (arrow) was apparent in the elutant from the TLQP-21-attached column. C, The ~30 kDa band was analysed by LC-MS/MS Orbitrap following trypsinisation. MS/MS fragmentation spectra show three unique peptides which have sequence identities to gC1qR. d, Transfection of siRNA against gC1qR (siRNA 1-4) into macrophages successfully reduced gC1qR protein expression. Non-specific negative control siRNA and did not alter the gC1qR expression. e, Transfection of siRNA against gC1qR into macrophages caused significant reduction in number of cells responding to TLQP-21. f, Pre-incubation (15 minutes) of macrophages with anti-gC1qR antibodies (MAb1, MAb2, 3 μg/ml each) significantly attenuates the TLQP-21-induced increase in intracellular Ca2+ levels.

Figure 7C:
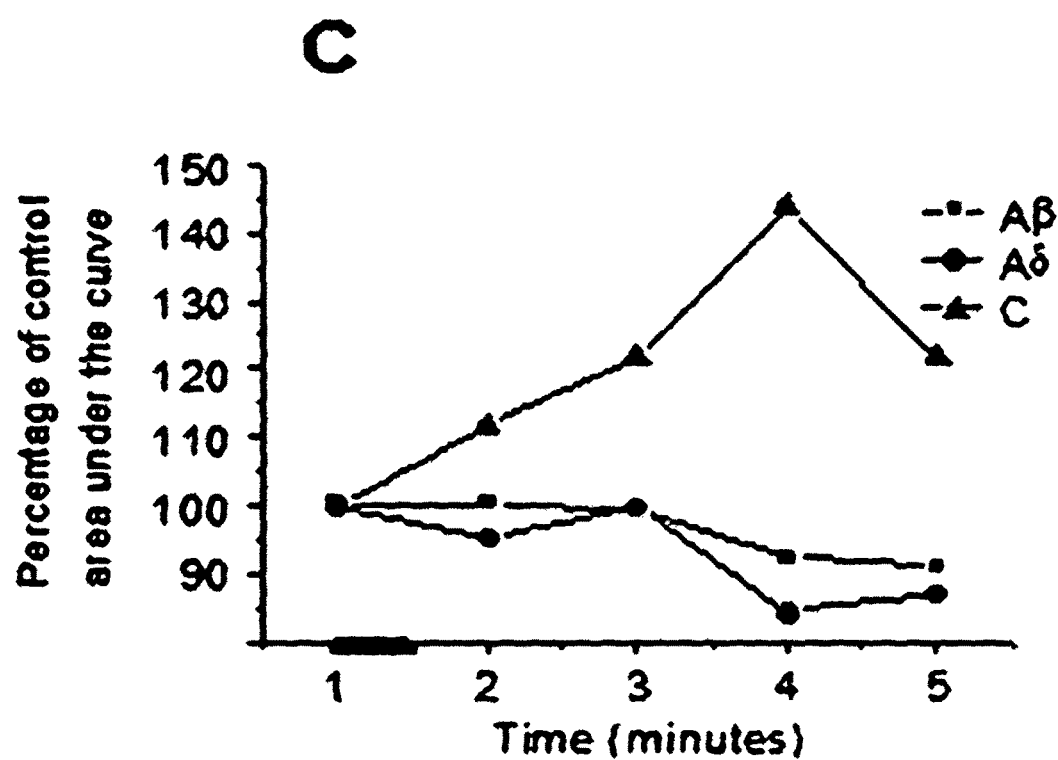

FIG. 7 LQEQ-19 sensitises nociceptors in vitro. (A) Typical average trace of 12 compound action potential recordings. The record was divided into 3 components according to the conduction velocities of Aβ fibres (6.2 m/s-2.1 m/s), Ad fibres (2.1 m/s-0.8 m/s) and C fibres (0.8 m/s-0.1 m/s) fibres. (B) Maximum amplitudes of Aβ, Ad and C components of compound action potentials. (C) Area under the curve of Aβ, Ad and C compound action potential. Bold line on the X axis indicates LQEQ-19 application FIG. 8: Hind paw injection of TLQP-21-treated macrophage produced tactile allodynia. Macrophages were treated with either 100 nM TLQP-21 or 100 nM scrambled TLQP-21 for 24 hours in culture. Following wash with PBS, macrophages (35,000 cells in 50 µl) were injected into the left hind paw. Ipsilateral paw withdrawal latency to Von Frey mechanical stimulation was measured at 1, 2, and 3 days after injection (n=9).

```
                                             SEQ ID NO: 1
Thr-Leu-Gln-Pro-Pro-Ala-Ser-Ser-Arg-Arg-Arg-His-

Phe-His-His-Ala-Leu-Pro-Pro-Ala-Arg-His-His-Pro-

Asp-Leu-Glu-Ala-Gln-Ala-Arg-Arg-Ala-Gln-Glu-Glu-

Ala-Asp-Ala-Glu-Glu-Arg-Arg-Leu-Gln-Glu-Gln-Glu-

Glu-Leu-Glu-Asn-Tyr-Ile-Glu-His-Val-Leu-Leu-His-

Arg-Pro

SEQ ID NO: 2
Leu-Gln-Glu-Gln-Glu-Glu-Leu-Glu-Asn-Tyr-Ile-Glu-

His-Val-Leu-Leu-His-Arg-Pro

SEQ ID NO: 3
Thr-Leu-Gln-Pro-Pro-Ala-Ser-Ser-Arg-Arg-Arg-His-

Phe-His-His-Ala-Leu-Pro-Pro-Ala-Arg
```

Figure 1:
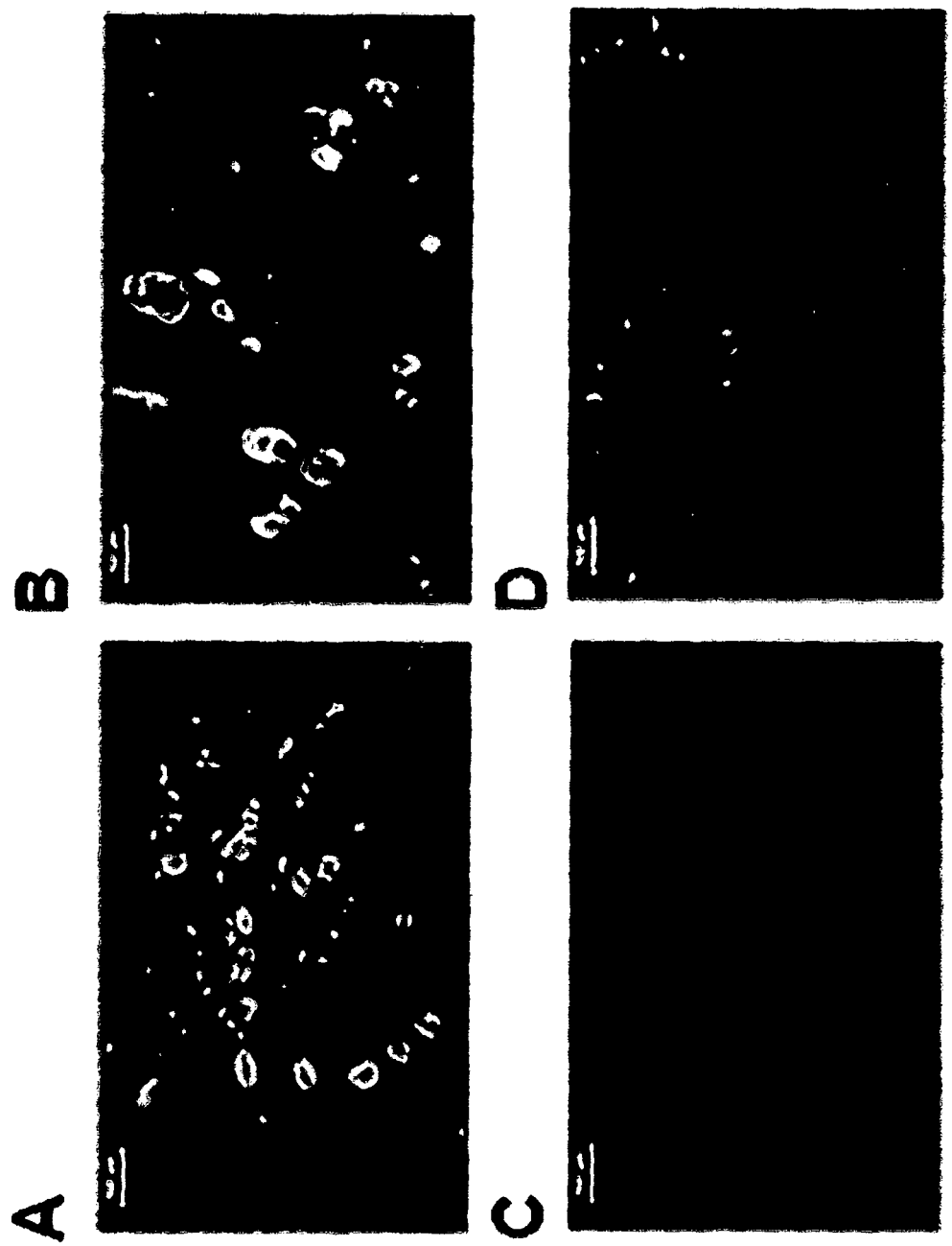
FIG. 1 Shows typical immunofluorescence images showing the presence of VGF peptide (light) in lumbar DRG neurons ipsilateral to A) VZV infection and B) L5 SNT, but not in C) uninfected fibroblast-injected control, nor D) sham-operated animals fourteen days after injury. Scale bar 100 μm. VGF-like immunoreactivity is increased in small diameter DRG neurons following varicella zoster infection and L5 spinal nerve transection.

The data generated indicates both mRNA and protein levels of VGF are upregulated in small diameter DRG neurons from rats following varicella zoster (VZV) infection (FIG. 1A) and L5 spinal nerve transection (FIG. 1B) compared to corresponding controls (FIG. 1C,D). This increased VGF-immunoreactivity in injured DRG neurons has been confirmed by other groups, as well as the upregulation of VGF-immunoreactivity in central terminals and their target dorsal horn neurons following nerve damage[19,20].

Our preliminary data showed that 100 nM TLQP-21(SEQ ID NO: 3), but not scrambled TLQP-21, TLQP-62 (SEQ ID NO: 1) nor LQEQ-19 (SEQ ID NO: 2), causes intracellular $Ca^{2+}$ increase in cultured macrophage visualised by Fluo-4 (FIG. 2), and this is due to $Ca^{2+}$ release from endoplasmic reticulum. The same phenomena were observed in cultured primary microglia.

Figure 2:
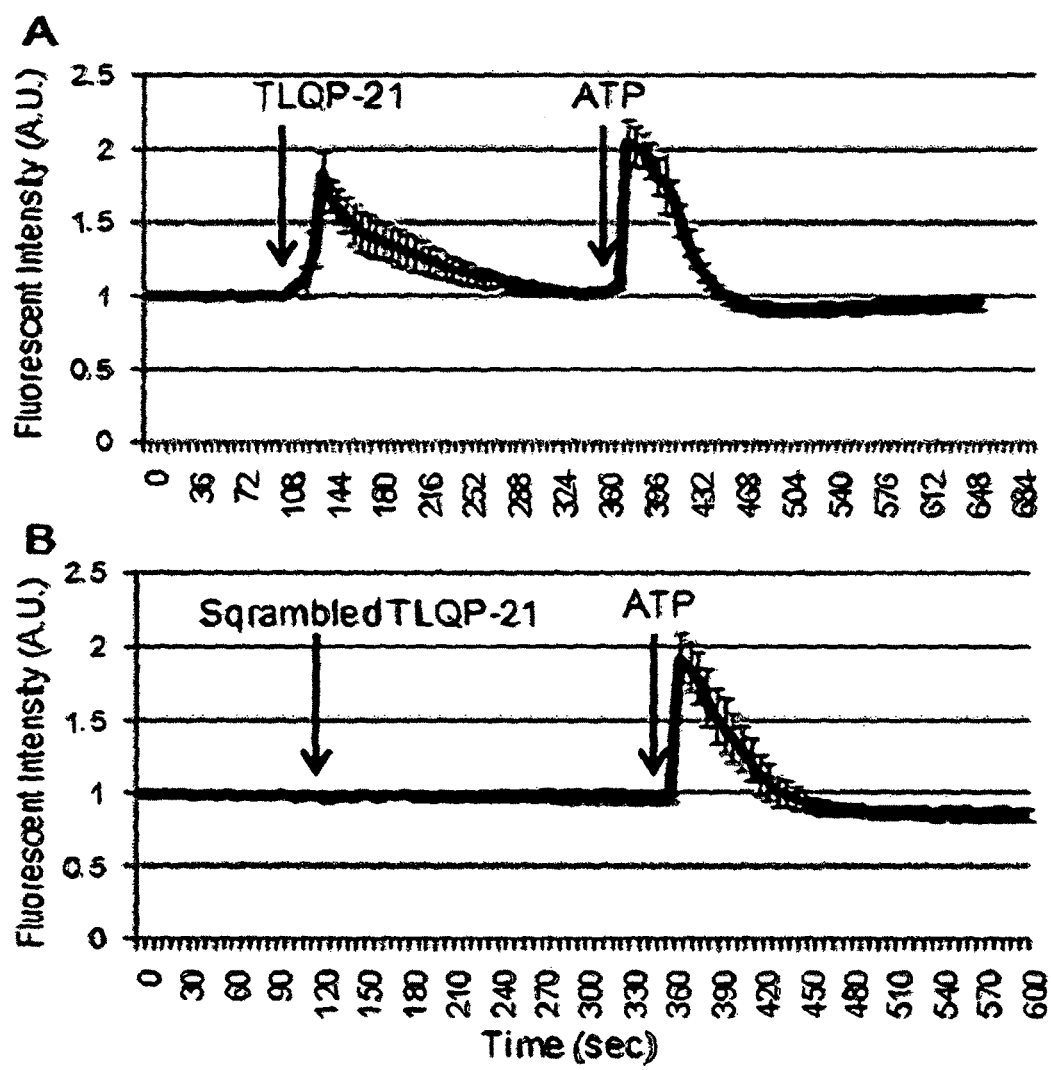
FIG. 2 Shows 100 nM TLQP-21 (A) but not scrambled TLQP-21 (B) elicits an increase in intracellular Ca2+ levels in cultured macrophages.
Figure 2A:
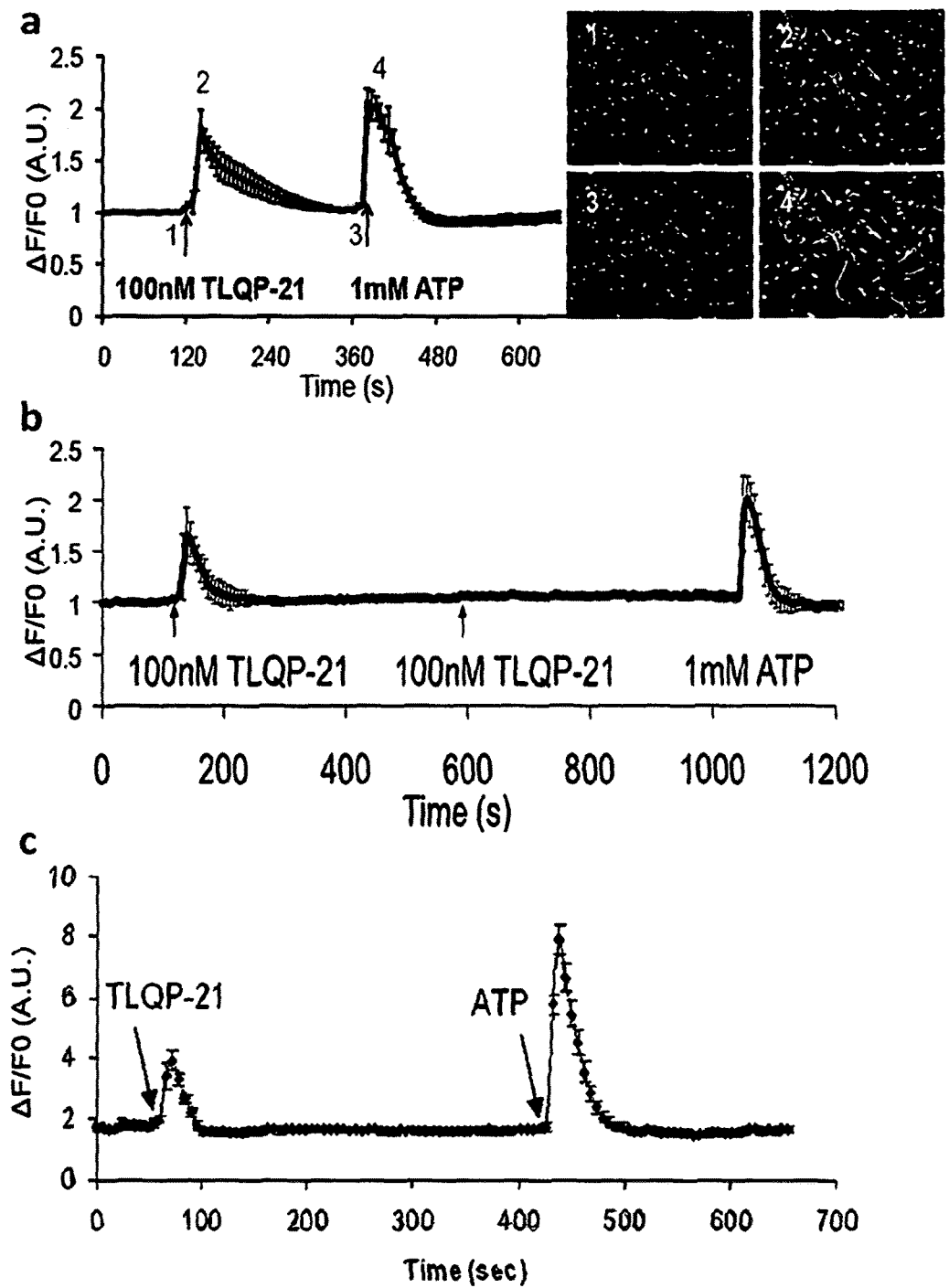
FIG. 2A TLQP-21 elicits intracellular Ca2+ increase in macrophages and microglia. a, Applying 100 nM TLQP-21 to cultured bone marrow-derived macrophages drives an increase in intracellular Ca2+, measured using Fluo-4. Cell images show the Fluo-4 fluorescence associated with different time points during the recording. 1 mM ATP was applied as a viability test, and only viable cells were selected for analysis. b, 100 nM TLQP-21 densensitises macrophage to further TLQP-21 stimulation, but not the ATP response. C, 100 nM TLQP-21 causes an increase in intracellular Ca2+ in cultured brain microglia.

TLQP-21 caused transient increase in intracellular Ca2+ levels in bone marrow-derived macrophages even at a concentration of 100 nM (FIG. 2A). This increase in intracellular Ca2+ levels elicited by TLQP-21 seems to be due to release of Ca2+ from their intracellular Ca2+ stores such as endoplasmic reticulum (ER) or mitochondria, because the Ca2+ increase is still observed when extracellular Ca2+ is depleted. A scrambled TLQP-21 (ScrTLQP-21) did not induce an increase in intracellular Ca2+ levels in these cells (supplementary figure). Interestingly, 100 nM TLQP-21 treatment induced de-sensitisation to subsequent TLQP-21 treatments, but not to ATP treatments (FIG. 2B). A possible explanation for the absence of a Ca2+ response from a second application of TLQP-21 is that there is a biological de-sensitisation occurring such as phosphorylation of the receptor. It is also possible that this could be due to depletion of Ca2+ in internal stores such as ER, however, this is less likely because the de-sensitisation occurs even with sufficient time (2 hours) to recover and replenish the Ca2+, and ATP treatment gave an increase in intracellular Ca2+ levels. Actually this de-sensitisation by TLQP-21 has also been observed in cerebellar granule cells. These observations suggest that the effect of TLQP-21 on macrophages and microglia cells is a specific biological response, and indicate presence of specific receptor for TLQP-21 in those cells. We also observed that brain microglia responded to TLQP-21 similarly to macrophages (FIG. 2C).

Our PCR array experiments revealed that chemokine Ccl11 is 2.78-fold upregulated in microglia upon TLQP-21 stimulation, whereas another chemokine Cxcl9 is 2.28-fold downregulated. Ccl11 has been linked to inflammation[23], while Cxcl9 is known as a natural antagonist to Ccl11 receptor CCR3[24]. We then used Sulfo-EMCS-conjugated TLQP-21 to purify and identify receptor(s) for TLQP-21. Whole brain tissue from post-natal day 4 rats was used, as this was the same tissue used to extract microglia for use in $Ca^{2+}$ imaging. The membrane fractions of rat brain was incubated with the crosslinker-conjugated TLQP-21, and analysed by Tricine-PAGE and Western blotting using Streptavidin-HRP for the biotin tag on TLQP-21. A ~30 kDa band appeared when the conjugated TLQP-21 was applied to the membrane preparation (FIG. 3A), but not in the membrane control (with Sulfo-EMCS crosslinker in the absence of TLQP-21). We also used biotin-tagged TLQP-21 and a monomeric avidin column to purify TLQP-21 binding proteins. The membrane fraction of rat brain was applied to a TLQP-21 attached column, and the elutions were analysed on SDS-PAGE and silver staining for direct comparison to the negative control (without TLQP-21). A ~30 kDa band (FIG. 3B, arrow) was also apparent with TLQP-21 attached to the column, but not in the corresponding negative control. The ~30 kDa bands from both gels were cut out, trypsinised and analysed using LC-MS/MS Orbitrap. A same protein was identified in the two distinct experiments with good peptide coverages, the receptor of the globular part of the complement protein C1q, designated gC1q-R. gC1q-R is an ubiquitous multiligand-binding protein involved in multiple cellular functions including inflammation and infection. gC1q-R is highly expressed in microglia and macrophage, and co-purified with TLQP-21. Pre-incubation of macrophage with 3 µg/ml of the neutralising gC1q-R monoclonal antibody for 15 minutes resulted in unresponsiveness to TLQP-21

To identify the receptor for TLQP-21, in addition to chemical cross-linking we employed mass spectrometry. The modified TLQP-21 was used with a biotin covalently attached via the amide bond at the N-terminus, and an extra cysteine residue was included at the C-terminus. Sulfo-EMCS cross-linker was conjugated to the modified TLQP-21 via the sulphydryl group of cysteine at the C-terminus. This cross-linker-conjugated TLQP-21 was able to induce an increase in intracellular Ca2+ levels similar to the wild type TLQP-21 (data not shown).

To elucidate the identity of the ~30 kDa protein, which were apparent in two different experiments, the protein band from the monomeric avidin experiment was analysed using LC-MS/MS Orbitrap. We identified three unique peptides which have sequence identities to gC1qR (FIG. 3C). The complement-binding protein, gC1qR is a highly acidic ~30 kDa protein, ubiquitously expressed and binds to the globular heads of C1q, the first subcomponent of the classical pathway for complement activation. It has been observed that gC1qR is a multi-functional protein (Ghebrehiwet and Peerschke, 2004). Western blot analysis confirms that the gC1qR protein appears at ~30 kDa in the elutions for the column with TLQP-21 attached, but not in the corresponding negative controls. Western blot also shows that macrophage and microglia cells express gC1qR.

Figure 4:
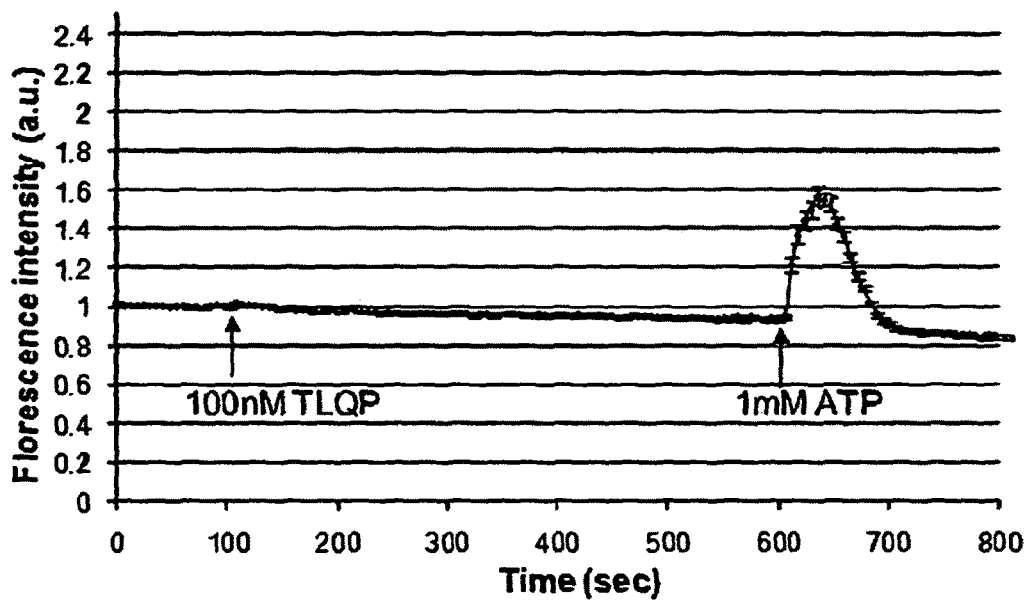
FIG. 4 Pre-treatment with the gC1q-R neutralising antibody (15 mins) attenuates the TLQP-21 induced Ca2+ increase in macrophages FIG. 5 Intraplantar injection of the LQEQ-19 (275 microgram) but not vehicle control was associated with a hypersensitivity to mechanical stimuli which developed in the ipsilateral hind limb, 10 minutes after injection. p≤0.001 vs vehicle ANOVA (Turkey)

(FIG. 4). This proves that gC1q-R is the receptor for TLQP-21, suggesting TLQP-21 acts on microglia and macrophage through gC1q-R and causes hyperactivity of DRG and/or spinal cord neurons.

Figure 5:
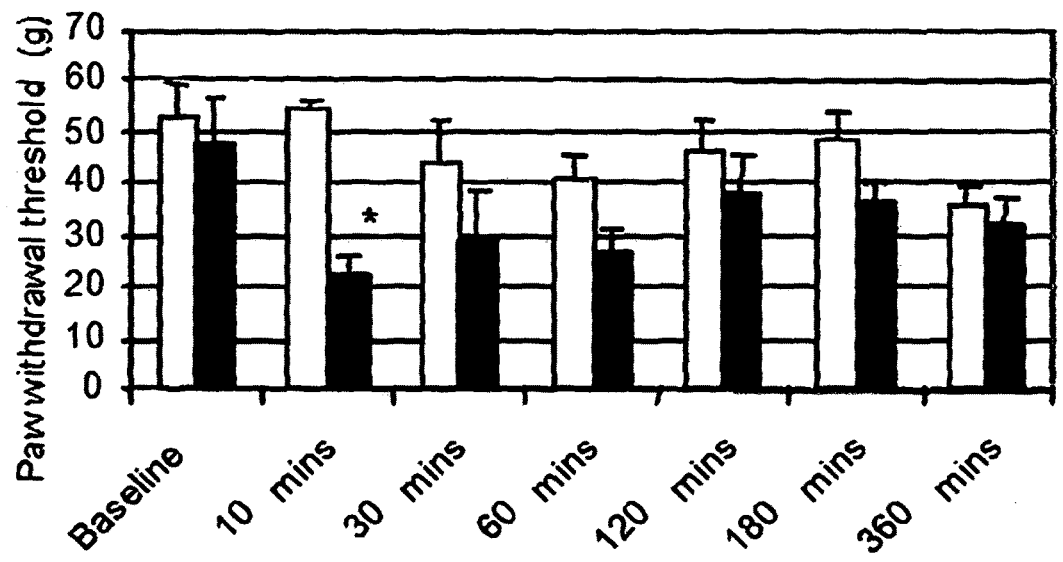

On the other hand, another VGF-derived peptide LQEQ-19 seems to have a direct role on DRG neurons. Intraplantar injection of LQEQ-19 in rats is associated with a hypersensitivity to mechanical stimuli (FIG. 5), and that application of LQEQ-19 to DRG significantly increases both the amplitude and the area under the curve of the C-fibre component of compound action potentials in dorsal roots (FIG. 6), suggesting that LQEQ-19 may act as an autocrine factor for nociceptive primary sensory neurons. In summary, there are at least three active VGF peptides involved in pain pathways, i.e., TLQP-62, TLQP-21 and LQEQ-19, and four types of cells, namely, spinal microglia, macrophage, nociceptive DRG neurons, and dorsal horn neurons, which respond to these peptides. In this project we will focus on the putative role of VGF peptides in regulating the activity/excitability of DRG neurons and the novel VGF-induced signaling pathway in microglia/macrophage.

Useful data have been obtained concerning the physiological functions of VGF peptides from mice subjected to targeted deletion of the VGF gene[19,25,26].

To Confirm the Cellular Pattern and Time Course of Expression of VGF and Associated Peptides in Primary Sensory Neurons in Models of Peripheral Neuropathic Pain:

We used co-localisation immunohistochemistry to examine the chronology and cellular pattern of VGF expression in DRGs harvested from animal models of neuropathic pain. A number of anti-VGF primary antibodies are now commercially available, and we initially screened them, including the polyclonal antibody that was used in the pilot experiments (FIG. 1), in hypothalamus (as a positive control), spinal cord and DRG from naive rats. We then used the optimal VGF antibody to study DRG and spinal cord expression of VGF in a model of traumatic neuropathy (L5 spinal nerve transection[27,28]), VZV-associated pain where rats are inoculated with VZV[11,29,30] and a model of HIV neuropathy where rats are treated with a combination of perineural HIV GP120 and systemic treatment with the antiretroviral drug Zalcitabine[6,10]. Animals were behaviourally characterised and only those showing a decrease in baseline hind limb withdrawal threshold to a mechanical stimulus >30% from baseline were used. In tissue taken from VZV infected animals additional co-localisation studies of VGF and the viral protein IE6211 may be performed in order to determine the cellular relationship between VZV infection and VGF immunoreactivity. Furthermore, the expression of VGF in DRGs from L5 spinal nerve transected animals was examined in both L5 and L4 DRGs to determine the relationship of VGF expression to peripheral nerve trauma of both injured and uninjured sciatic neurons[31]. To determine the chronology of VGF expression this will be performed at a number of time points after the creation of neuropathy. Experience from previous studies indicate that we require a group size of n=6 for histological studies. We will also perform western blotting and qRT-PCR for quantitative analysis of VGF expression in DRG in these pain model animals.

Analysis the promoter region of VGF gene responsible for activation triggered by nerve damage was performed. Our preliminary experiment identified that the 853 bp upstream sequence of VGF gene possesses functional promoter region. We further characterised the promoter region responsive to nerve damage and inflammation by deletion analysis. A series of VGF promoter-Luciferase constructs containing different length of the VGF promoter region were MicroPorated into cultured DRG neurons. The promoter activity in response to various noxious stimuli such as NGF and gp120 was be studied and the essential promoter element(s) was be identified. We then examined the involvement of the element(s) in VGF expression by introducing site-directed mutations to the element(s). The wild type- and mutant-VGF promoter-Luciferase constructs were then be cloned into replication-defective vectors based on herpes simplex virus (HSV). It has been recently reported that HSV vectors show high transduction efficiency in DRG neurons in vivo[32]. We injected the HSV vector containing wild type- and mutant-VGF promoter-Luciferase complex into the tibial nerve of Wister rats (once daily, 5 µl). A GFP expression vector was co-injected to monitor transduction efficiency. The rats were subjected to three neuropathic pain models mentioned above, and the Luciferase activity of each VGF promoter constructs in DRG neurons will be analysed by luminometer after extracting the DRGs from rats.

To Investigate Consequences of VGF siRNA Application in Neuropathic Pain Models:

We searched for the most potent siRNA sequence to downregulate the VGF protein expression in cultured DRG neurons using real-time qRT-PCR and immunocytochemistry as validation methods. According to our experience[33], at least one out of three siRNA sequences efficiently suppressed the target protein expression. Once the siRNA sequence was determined, we observed the in vivo effect of siRNA treatment in all three models of neuropathic pain via intrathecal injection method (VGF-specific siRNA, the scrambled control siRNA, or a vehicle control) as we previously showed successful downregulation of a specific gene expression in DRG in vivo[34]. Injections were carried out both at the time of the induction of the neuropathy and once the neuropathy is established (power calculation indicates a group size of n=12). The effect of siRNA on naïve and appropriate sham treated animals for each model was also assessed. The behavioural/sensory threshold experiments were conducted in the same fashion as described in aim 1. We will also assess the animals for anxiety-like behaviour (thigmotaxis)[9-11,35].

Transfection of siRNAs against gC1qR into macrophages also significantly reduced the protein levels of gC1qR (FIG. 3D) and the number of cells responding to TLQP-21 (FIG. 3E). Pre-incubation of macrophages for 15 mins with neutralising gC1qR monoclonal antibodies resulted in significant reduction of the response to TLQP-21 (FIG. 3F). These data prove that gC1qR is the receptor for TLQP21.

To Study Efficacy and Potency of VGF Derived Peptides in Nociception:

Currently, 13 VGF-derived peptides have been identified. Although our preliminary data demonstrated that LQEQ-19 sensitises nociceptors in vitro and causes a mechanical hypersensitivity in vivo, and TLQP-21 causes $Ca^{2+}$ increase in microglia/macrophage leading to transcriptional regulations of chemokines, there may be other VGF peptides with more potent effect on sensory thresholds. A longer VGF peptide (TLQP-62) induces pain behaviour (cold and mechanical hypersensitivity) when administered intrathecally in nanomolar concentrations[19]. TLQP-62 and AQEE-30 were found to increase synaptic activity in the hippocampal neurons[22], while QAEA-38 (also known as NERP-2) is involved in physiological regulation of water homeostasis[36]. Furthermore, LQEQ-19 causes P38 MAP kinase phosphorylation in microglia[20] and enhances pain behaviour in the formalin test[17] and also biological activity in other physiological systems[37-39].

In vitro studies: In order to identify the most potent VGF peptide in activating DRG neurons and microglia/macrophage, we will screen up to ten VGF-derived peptides in vitro. These peptides were either commercially sourced or provided by Neusentis/Pfizer. The effects of VGF peptides on sensory neurons was analysed using whole-cell current-clamp recordings on cultured DRG neurons. Responses of cells to depolarising current pulses will be analysed before and after superfusion of peptides and their efficacy and potency established. The nociceptive phenotype of the cells was confirmed by superfusing capsaicin to the cells at the end of the recordings, and analysing the action potential and current threshold of the cells. Based on our pilot data with LQEQ-19, we expected that some of these peptides will increase the activity of nociceptive neurons. The activation of microglia and macrophage was studied on two parameters, intracellular $Ca^{2+}$ increase and P38 MAP kinase phosphorylation. Intracellular $Ca^{2+}$ levels will be monitored using fluo-4 under a confocal microscope as shown in FIG. 2 and FIG. 4. The phosphorylation levels of P38 MAP kinase was investigated as shown before[20]. Once we identified peptides capable of activating sensory neurons and/or microglia/macrophage, confirmed the specific effects using scrambled peptides.

In vivo experiments: Having identified "lead" VGF peptides in vitro (above), we investigated their properties in vivo, using 2 strategies. Acute experiments: Initially, we administered the peptides by intraplantar and intrathecal injection to male Wistar rats and determine the effect of the peptide on mechanical, cold and thermal sensory thresholds for limb withdrawal and spontaneous foot lifting/licking, over two hours[19]. Three point dose response curves was constructed and a vehicle control group included. Chronic experiments: Once the optimal peptide and concentration have been determined we will examine the effect of prolonged application of two "lead" VGF peptide to the sciatic nerve and spinal cord of male Wistar rats using an implanted osmotic mini-infusion Alzet pump attached to a perineural and intrathecal catheter for infusion over 14 days[40]. We have previously demonstrated the utility of perineural administration in other models of peripheral neuropathic pain[9,10]. Again, three doses were administered and there was a vehicle control group, with randomisation and blinding. We monitored hind-limb withdrawal thresholds/latency to static and dynamic mechanical stimuli as well as thermal and cool stimuli[9-11,27] over 28 days and compare these to baseline values. We will also monitored the animals for spontaneous foot lifting/licking and anxiety-like behaviour (thigmotaxis) in the open field paradigm at day 14[9-11,35]. At the end of these experiments (28 days) and smaller cohorts (7 and 14 days) the animals were culled, perfused fixed and the DRGs and spinal cord harvested for the immunohistochemical studies detailed below.

Figure 6:
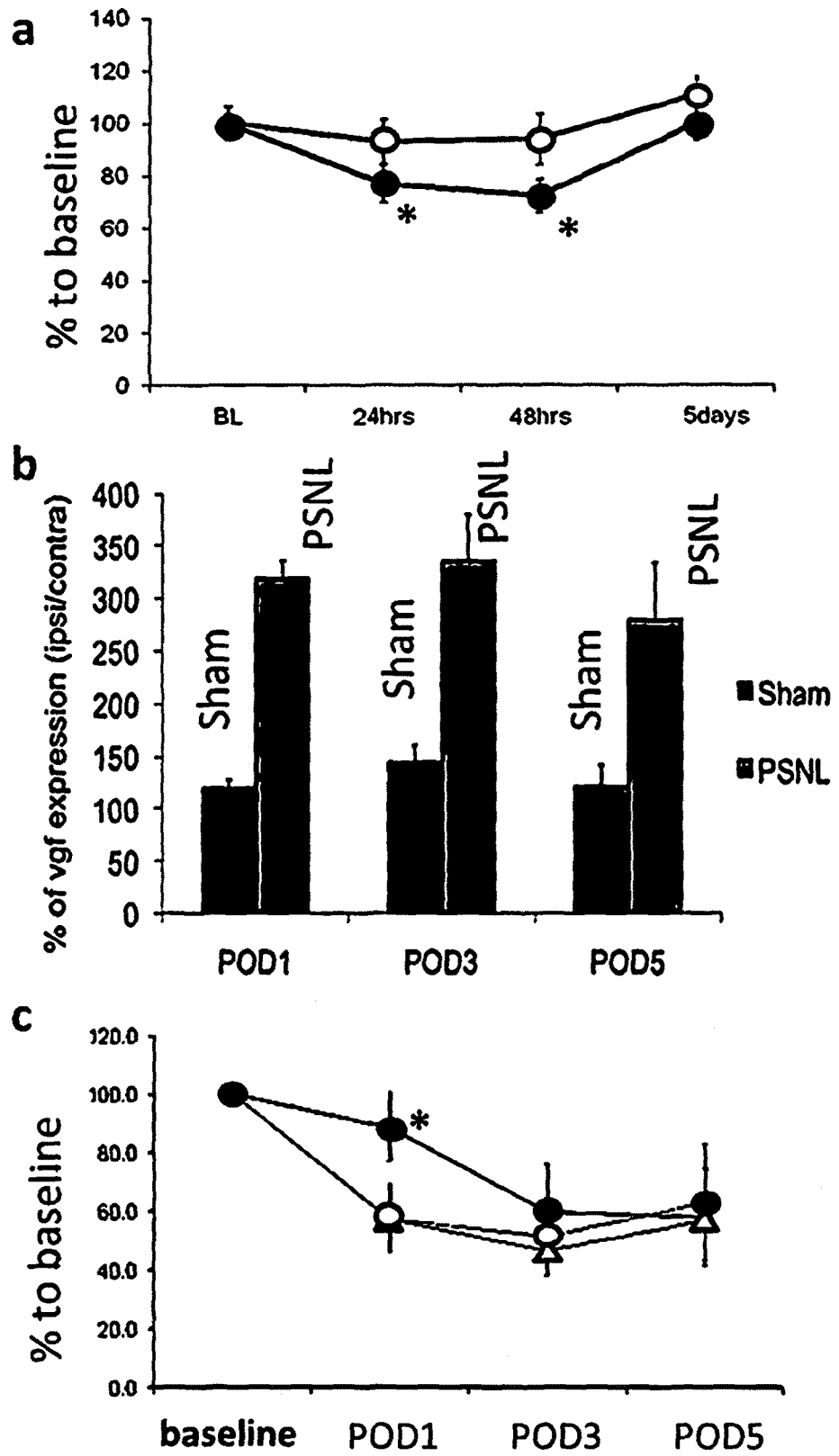
FIG. 6A-C Intraplantar injection of macrophages stimulated with TLQP-21 can evoke mechanical hypersensitivity, and anti-gC1qR antibody reverses mechanical hypersensitivity in partial sciatic nerve ligation (PSNL) model. a, 80,000 macrophages treated with 100 nM TLQP-21 (closed circle) and scrambled TLQP-21 (open circle) for 24 hours have been intraplantarly injected into 3 weeks old male rats. Mechanical sensitivity was examined by electrical Von Frey test. Injection of macrophages stimulated with TLQP-21 caused reduction of paw withdrawal thresholds at 24 and 48 hours after injection. Mean±s.e.m. *P<0.05 vs scrambled TLQP-21. b, qRT-PCR revealed significant upregulation of VGF mRNA in DRG of partial sciatic nerve ligation (PSNL) model rats. C, Time course of paw withdrawal thresholds to Von Frey mechanical stimulation on an left hind paw of PSNL model rats. The left sciatic nerve was exposed, tied with non-absorbable silk thread, and wrapped loosely with a oxidized regenerated cellulose previously soaked in 200 µl of PBS (open triangle) or PBS containing 25 µg of anti-gC1qR (closed circle) or control antibodies (open circle). Application of anti-gC1qR antibody significantly attenuated the hypersensitivity caused by PSNL 1 day after the surgery. Mean±s.e.m. *P<0.05 vs controls.

We hypothesised that macrophages stimulated by TLQP-21 affects sensory neurons and alter the mechanical sensitivity. We tested this hypothesis by measuring paw withdrawal thresholds in normal rats after hind paw injection of cultured macrophages that had been pre-treated with either TLQP-21 or ScrTLQP-21 for 24 hours. ScrTLQP-21 treated macrophages injection did not affect the paw withdrawal threshold. In contrast, the paw withdrawal threshold decreased markedly 24 hours after the injection of macrophages stimulated by TLQP-21 (FIG. 6). This effect lasted for 48 hours after injection. We then examined if VGF mRNA is upregulated in DRG of partial sciatic nerve ligation (PSNL) model rats. qRT-PCR revealed that VGF mRNA is significantly upregulated in our PSNL model (FIG. 3b). This data strongly support the previous observations VGF is a commonly upregulated molecule in chronic pain models. We then examined if in vivo application of the neutralising gC1qR antibody can prevent or delay development of neuropathic pain in PSNL model rats. The gC1qR antibody was applied to the site next to nerve ligation, in a cellulose membrane soaked form. After 24 hours of PSNL, vehicle and control IgG treated rats showed dramatic reduction of mechanical threshold measured by Von Frey mechanical stimulation. In contrast, application of the gC1qR antibody substantially attenuated the hypersensitivity caused by PSNL. These results suggest that macrophages stimulated by TLQP-21 via its receptor gC1qR cause hyperexcitation of sensory neurons.

As its name suggests, gC1qR was originally identified as a protein with high affinity for the globular heads of the complement component C1q. It is, however, now known to be able to interact with a large variety of ligands. gC1qR is a 33 kDa, highly acidic, and ubiquitously expressed protein. It has a doughnut-shaped trimer structure, and can form a disulfide bond between monomers of different gC1qR trimers, resulting in a hexameric structure (Jiang et al. 1999). It was observed that fibroblasts expressing gC1qR, after application of the complement C1q protein, induced a rapid and transient increase in intracellular Ca2+ levels via an IP3-dependent pathway (Bordin et al. 1998). It has been observed that gC1qR can bind both high molecular weight kininogen (HK) and factor XII, and more recently it was observed that the HK-gC1qR interaction plays an important role in bradykinin generation in macrophages (Barbasz et al. 2008). Thus, the gC1qR protein, particularly when on the cell surface, can bind plasma proteins such as C1q and HK, which in turn generates an inflammatory response from both the complement and kinin/kallikrein systems and initiates a plethora of biological responses. Macrophages secrete diverse signaling molecules such as cytokines, chemokines, and growth factors, which can sensitise sensory neurons. It would be interesting to see if any particular cytokines are dysregulated in macrophages upon TLQP-21 stimulation, and such cytokines may have direct effects on hypersensitivity of sensory neurons. It is also important to study how TLQP-21-mediated activation of microglia relates to P2X-mediated mechanical allodynia.

Although roles of macrophages in inflammatory pain have been well documented, involvement of macrophages in neuropathic pain signaling has not been studied in detail.

There is firm evidence that resident macrophages in DRG proliferate after nerve injury (Mueller et al. 2001), and circulating monocytes are recruited into the site of injury (Abbadie et al. 2003). Systemic depletion of macrophages reduces mechanical hypersensitivity after peripheral nerve injury (Liu et al. 2000). It has also been shown that depletion of macrophages delays progression of neuropathic pain in diabetic model rats (Mert et al. 2009).

The present data suggest that disrupting TLQP-21-gC1qR interaction and/or its downstream signaling may provide a new way of controlling chronic pain.

To Identify the Mechanisms Involved in the VGF-Evoked Activation of Primary Sensory Neurons, Spinal Microglia and Macrophage:

Previous data indicate that VGF-derived peptides activate various intracellular signaling molecules, including the extracellular signal-regulated kinase 1/2 (ERK1/2) and protein kinase B (PKB/Akt) in neurons[39]. ERK1/2 and PKB/Akt have been shown to modify the activity of membrane molecules in neurons including the delayed rectifier $K^+$ channel and the noxious heat transducer TRPV1, which result in increased activity of the cells[41-43]. It is also reported that there is an increase of phosphorylated p38 MAP kinase in spinal microglia of mice injected intrathecally with LQEQ-19[20]. Here, we studied the activation of primary sensory neurons by recording whole-cell currents and identifying the membrane and intracellular signaling molecules involved in the VGF-derived peptide-induced increase in the activity of DRG neurons. Initial assessment of voltage-gated channels affected by VGF-derived peptide(s) was performed by activating the channels by a simple voltage protocol. Depending on the results of the initial assessment, the effect of VGF-derived peptide(s) will be studied on $Na^+$, $K^+$ and $Ca^{2+}$ currents isolated by ionic substitution, biophysical methods and/or pharmacology. The nociceptive phenotype of the cells was confirmed by applying capsaicin at the end of the recordings. In DRGs from VGF peptide-treated animals (aim 3, chronic experiments) we will perform immunohistochemistry for markers known to be dysregulated in neuropathy including markers of neuronal stress and regeneration, apoptosis and drug targets (e.g. ATF3, GAP43, caspase-3, c-Jun, galanin, neuropeptide Y, selected $Na^+$ channels, $\alpha_2\delta_1$ $Ca^{2+}$ channel subunits). To determine the phenotype of cells expressing these markers we performed a cell size analysis combined with co-localisation studies using established markers of DRG cell phenotype (e.g. NeuN, peripherin, NF-200, TRPV1, IB4, CGRP and non-neuronal cells GFAP and Iba-1) using antibodies we have successfully used in previous studies[9,10,44,45].

Two transducer molecules, TRPV1 and the cold-sensitive TRPA1 have been implicated[46,47] in the development of nerve injury-associated pain. Therefore, here we also assessed the effect of VGF-derived peptide(s) on the excitability of TRPV1 and TRPA1 using whole-cell voltage-clamp recordings from cultured primary sensory neurons and by activating these receptors by their specific and selective activators, capsaicin (100 nM) and cinnamaldehyde (100 µM), respectively. Studies on signaling molecules involved in VGF peptide-induced changes will involve measuring the activity of membrane molecules which are affected by the peptide(s). Here, MEK (e.g. PD 98059), phosphatidylinositol 3-kinase (e.g. LY294002), and p38 MAPK (e.g. SB202190) inhibitors will be used to elucidate whether PKB/Akt, ERK1/2, and/or p38 MAPK are involved in the effect. The VGF peptides identified in Aim 1 was be applied at 75% of the EC50 determined during the current-clamp recordings for 1 minute in all experiments.

Our preliminary data shows TLQP-21 increases $Ca^{2+}$ release from endoplasmic reticulum in microglia and macrophage (FIG. 2). We investigated the involvement of IP3 and characterisation of phospholipase C (PLC) which is responsible for the IP3 production in microglia/macrophage upon TLQP-21 stimulation using siRNA specific to isozymes of PLC. Once the PLC involved in TLQP-21-evoked $Ca^{2+}$ release was identified, we further investigated the upstream signaling mechanism of the PLC. From this angle, we were able to narrow down the candidate receptors for TLQP-21. The downstream signaling of the $Ca^{2+}$ release was studied by analysing expression levels of multiple markers for microglia/macrophage activation such as P2X4, P2X7, P2Y6, Kv1.3, BDNF and chemokines by qRT-PCR. In a similar way, we also investigated the p38 MAP kinase cascade in microglia in response to LQEQ-19 stimulation. We also used a DNA microarray to investigate differences in mRNA expression between TLQP-21 and scrambled TLQP-21 stimulated microglia and macrophage (n=4 at four different time points). The authenticity of gC1q-R as a TLQP-21 receptor was further investigated by gC1q-R siRNA electroporation into cultured microglia and macrophage.

1. Scott F. T. et al J Med Virol 2003; 70 Suppl 1:S24-S30.
2. Gauthiera A. et al Epidemiology and Infection 2009; 137(01):38-47.
3. Smyth K. et al HIV Med 2007; 8:367-373.
4. Hempenstall K. et al Public Library of Science-Medicine 2005; 2:628-644.
5. Finnerup N. B. et al Pain 2005; 118:289-305. 6. Maratou K. et al European Journal of Pain 2009; 13(4):387-398.
7. Costigan M. et al BMC Neuroscience 2002; 3:16.
8. Xiao H. S. et al Proceedings of the National Academy of Sciences 2002; 99:8360-8365.
9. Wallace V. C. J. et al Pain 2007; 133:47-63.
10. Wallace V. C. J. et al Brain 2007; 130:2688-2702.
11. Hasnie F. S. et al Neuroscience 2007; 144:1495-1508.
12. Levi A. et al Science 1985; 229:393-395.
13. Salton S. R. et al Front Neuroendocrinol 2000; 21:199-219.
14. Levi A. et al Cellular and Molecular Neurobiology 2004; 24:517-533.
15. Eagleson K. L. et al J Neurosci 2001; 21:9315-9324.
16. Snyder S. E. et al Brain Res Mol Brain Res 1997; 49:307-311.
17. Rizzi R. et al Neuroscience Letters 2008; 441:129-133.
18. Ferri G. L. et al Brain Res Mol Brain Res 1992; 13:139-143.
19. Moss A. et al Molecular Pain 2008; 4:62.
20. Riedl M. S, et al J Neurosci 2009; 29(42):13377-13388.
21. Possenti R. et al EMBO J 1989; 8:2217-2223. 22. Alder J. et al J Neurosci 2003; 23:10800-10808.
23. Waddell A. et al J Immunol 2011; 186(10):5993-6003.
24. Loetscher P. et al J Biol Chem 2001; 276: 2986-2991.
25. Hahm S. et al Neuron 1999; 23:537-548.
26. Watson E. et al Endocrinology 2005; 146:5151-5163.
27. Bridges D. et al Br J Pharmacol 2001; 133:586-594.
28. Kim S. H., Chung J. M. Pain 1992; 50:355-363.
29. Fleetwood-Walker S. M. et al J Gen Virol 1999; 80:2433-2436.
30. Garry E. M. et al Pain 2005; 118:97-111.
31. Hudson L. J. et al Eur J Neurosci 2001; 13:2105-2114.
32. Anesti A. M, et al Nucleic Acids Res 2008; 36(14):e86.
33. Shao D. et al Mol Cell Neurosci 2009; 42(3):219-225.
34. Baker M. D. et al Mol Cell Neurosci 2011; 48(3):258-265.

35. Wallace V. C. J. et al Br J Pharmacol 2007; 151:1117-1128.
36. Toshinai K, Nakazato M. Cell Mol Life Sci 2009; 66(11-12):1939-1945.
37. Bartolomucci A. et al Proc Natl Acad Sci USA 2006; 103:14584-14589.
38. Jethwa P. H. et al Endocrinology 2007; 148:4044-4055.
39. Severini C. et al J Neurochem 2008; 104:534-544.
40. Lever I. J. et al Br J Pharmacol 2007; 151:292-302.
41. Zhu W., Oxford G. S. Mol Cell Neurosci 2007; 34:689-700.
42. Zhuang Z. Y. et al J Neurosci 2004; 24:8300-8309.
43. Kayssi A. et al J Physiol 2007; 580:977-991.
44. Bridges D. et al Neuroscience 2003; 119:803-812.
45. Farquhar-Smith W. P. et al Mol Cell Neurosci 2000; 15:510-521.
46. Obata K. et al J Clin Invest 2005; 115(9):2393-2401.
47. Christoph T. et al Neurochem Int 2007; 50(1):281-290.

The invention claimed is:

1. A method of treating neuropathic pain, comprising administering a therapeutically effective amount of an inhibitor of VGF activity resulting from binding of VGF or a TLQP-21 peptide to a gC1qR receptor,
    wherein TLQP-21 peptide comprises a peptide having the amino acid sequence set forth in SEQ ID NO:3,
    wherein the inhibitor is specific to VGF, the TLQP-21 peptide, or gC1qR, and
    wherein the inhibitor is an antibody or a binding fragment thereof.

2. The method of claim 1, wherein the neuropathic pain comprises neuropathic pain associated with nerve injury or damage, posttherapeutic neuropathy, HIV/AIDS, diabetic neuropathy, fibromyalgia, alcohol neuropathy, amputation, facial nerve problems, wherein the facial nerve problems comprise Bell's Palsy, cancer, multiple sclerosis, compres-

SEQUENCE LISTING

<160> NUMBER OF SEQ ID NOS: 3

<210> SEQ ID NO 1
<211> LENGTH: 62
<212> TYPE: PRT
<213> ORGANISM: Artificial
<220> FEATURE:
<223> OTHER INFORMATION: TLQP-62 peptide from VGF

<400> SEQUENCE: 1

Thr Leu Gln Pro Pro Ala Ser Ser Arg Arg Arg His Phe His His Ala
1               5                   10                  15

Leu Pro Pro Ala Arg His His Pro Asp Leu Glu Ala Gln Ala Arg Arg
            20                  25                  30

Ala Gln Glu Glu Ala Asp Ala Glu Glu Arg Arg Leu Gln Glu Gln Glu
        35                  40                  45

Glu Leu Glu Asn Tyr Ile Glu His Val Leu Leu His Arg Pro
    50                  55                  60

<210> SEQ ID NO 2
<211> LENGTH: 19
<212> TYPE: PRT
<213> ORGANISM: Artificial
<220> FEATURE:
<223> OTHER INFORMATION: LQEQ-19 peptide from VGF

<400> SEQUENCE: 2

Leu Gln Glu Gln Glu Glu Leu Glu Asn Tyr Ile Glu His Val Leu Leu
1               5                   10                  15

His Arg Pro

<210> SEQ ID NO 3
<211> LENGTH: 21
<212> TYPE: PRT
<213> ORGANISM: Artificial
<220> FEATURE:
<223> OTHER INFORMATION: TLQP-21 peptide from VGF

<400> SEQUENCE: 3

Thr Leu Gln Pro Pro Ala Ser Ser Arg Arg Arg His Phe His His Ala
1               5                   10                  15

Leu Pro Pro Ala Arg
            20 sion of a nerve by a tumor, diabetes, stroke or excessive inflammatory responses that result in tissue damage.

3. The method of claim 1, wherein the inhibitor blocks binding of VGF or the TLQP-21 peptide to the receptor gC1qR,
   wherein the TLQP-21 peptide comprises a peptide having the amino acid sequence set forth in SEQ ID NO:3.

4. The method of claim 1, wherein the inhibitor blocks signalling subsequent to binding of VGF or the TLQP-21 peptide to the receptor gC1qR,
   wherein the TLQP-21 peptide comprises a peptide having the amino acid sequence set forth in SEQ ID NO:3.

5. The method of claim 1, wherein the antibody is specific to VGF and an activity thereof associated with binding to gC1qR.

6. The method of claim 1, wherein the antibody is specific for the receptor gC1qR and the activity thereof associated with binding VGF or the TLQP-21 peptide,
   wherein the TLQP-21 peptide comprises a peptide having the amino acid sequence set forth in SEQ ID NO:3.

7. The method of claim 1, wherein the neuropathic pain is nociceptive pain.

8. The method of claim 1, wherein the neuropathic pain is allodynia.

9. The method of claim 1, wherein the neuropathic pain is continuous.

10. The method of claim 1, wherein the neuropathic pain is episodic.

11. The method of claim 1, wherein the neuropathic pain is peripheral.

12. The method of claim 1, wherein the neuropathic pain is central.

\* \* \* \* \*